US 11,369,788 B2

(12) United States Patent
Dubuclet et al.

(10) Patent No.: US 11,369,788 B2
(45) Date of Patent: Jun. 28, 2022

(54) STIMULATION LEAD AND METHOD INCLUDING A MULTI-DIMENSIONAL ELECTRODE ARRAY

(71) Applicant: ADVANCED NEUROMODULATION SYSTEMS, INC., Plano, TX (US)

(72) Inventors: Jodi T. Dubuclet, Dallas, TX (US); Cory Brinkman, Celina, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 830 days.

(21) Appl. No.: 15/631,127

(22) Filed: Jun. 23, 2017

(65) Prior Publication Data

US 2018/0369574 A1  Dec. 27, 2018

(51) Int. Cl.
*A61N 1/05* (2006.01)

(52) U.S. Cl.
CPC .................................. *A61N 1/0553* (2013.01)

(58) Field of Classification Search
CPC .................................................... A61N 1/0553
See application file for complete search history.

(56) References Cited

U.S. PATENT DOCUMENTS

| 6,529,774 | B1 * | 3/2003 | Greene .................... A61B 5/24 600/545 |
| 7,212,110 | B1 | 5/2007 | Martin et al. |
| 7,228,179 | B2 | 6/2007 | Campen et al. |
| 7,571,007 | B2 | 8/2009 | Erickson et al. |
| 8,244,374 | B1 | 8/2012 | Swanson |
| 8,271,099 | B1 | 9/2012 | Swanson |
| 9,084,882 | B1 * | 7/2015 | Raines ................. A61N 1/0553 |
| 2006/0170486 | A1 | 8/2006 | Tranchina et al. |

(Continued)

FOREIGN PATENT DOCUMENTS

| WO | 2001093953 A1 | 12/2001 |
| WO | 2008024524 A1 | 2/2008 |

OTHER PUBLICATIONS

Int'l Search Report and Written Opinion, dated Sep. 26, 2018—PCT/US2018/039075.

(Continued)

*Primary Examiner* — Lynsey C Eiseman
*Assistant Examiner* — Jessandra F Hough
(74) *Attorney, Agent, or Firm* — The Small Patent Law Group LLC; Dean D. Small

(57) ABSTRACT

Stimulation lead includes an elongated lead body having distal and proximal ends and wire conductors extending therebetween. The stimulation lead also includes a lead paddle having a multi-dimensional array of electrodes positioned along a contact side of the lead paddle. The electrodes are electrically coupled to the wire conductors. The lead paddle includes a paddle body and a conductor organizer disposed within the paddle body. The conductor organizer has multiple channels extending along the lead paddle. The channels receive the wire conductors and retain the wire conductors in a designated arrangement with respect to the lead paddle. The conductor organizer has openings to the channels. The wire conductors extend through the openings and are terminated to the respective electrodes.

18 Claims, 15 Drawing Sheets

(56) References Cited

U.S. PATENT DOCUMENTS

| | | | |
|---|---|---|---|
| 2007/0191709 A1* | 8/2007 | Swanson | A61N 1/0553 |
| | | | 600/433 |
| 2008/0046051 A1* | 2/2008 | Skubitz | A61N 1/0553 |
| | | | 607/115 |
| 2008/0228250 A1 | 9/2008 | Mironer | |
| 2011/0238145 A1* | 9/2011 | Swanson | A61N 1/0551 |
| | | | 607/116 |
| 2012/0143296 A1* | 6/2012 | Pianca | A61N 1/0558 |
| | | | 607/116 |
| 2016/0067477 A1 | 3/2016 | Dubuclet | |
| 2017/0080213 A1 | 3/2017 | Wright et al. | |

OTHER PUBLICATIONS

Int'l Search Report and Written Opinion, dated Oct. 4, 2018—PCT/US2018/039083.
Restriction Requirement, dated Mar. 14, 2019—Related U.S. Appl. No. 15/631,140.

\* cited by examiner

STIMULATION LEAD AND METHOD INCLUDING A MULTI-DIMENSIONAL ELECTRODE ARRAY

BACKGROUND OF THE INVENTION

Embodiments herein generally relate to stimulation therapy, such as spinal cord stimulation (SCS) therapy, and more particularly to systems and methods including a paddle lead having a multi-dimensional electrode array.

Stimulation systems are devices that generate electrical pulses and deliver the pulses to tissue to treat a variety of disorders. Neurostimulation (NS) is the stimulation of nerve tissue, such as the spinal cord or brain. SCS is a common type of neurostimulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can be used to mask certain types of pain transmitted from regions of the body associated with the stimulated nerve tissue. SCS may have applications other than pain alleviation as well.

NS systems, including SCS systems, generally include a pulse generator and one or more leads electrically coupled to the pulse generator. A lead includes a lead body having insulative material and an electrode array that is arranged at an end of the lead body. The electrodes are electrically coupled to the pulse generator through wire conductors. The lead is implanted within an individual's body such that the electrode array is proximate to nervous tissue (e.g., within epidural space of a spinal cord) to deliver the electrical pulses. The pulse generator may also be implanted within the individual and may be programmed (and re-programmed) to provide the electrical pulses in accordance with a designated sequence.

Typically, there are two types of leads that can be used. The first type is a percutaneous lead, which has a rod-like shape and includes electrodes spaced apart from each other along a single axis. The second type of lead is a paddle lead. A paddle lead has an elongated multi-dimensional body at an end of the lead that has a thin, rectangular-like shape (i.e., paddle-like shape). Although the percutaneous lead may include only one row or column of electrodes, the paddle lead includes an array of electrodes that are spaced apart from each other along more than one dimension. The wire conductors that deliver the electrical signals from the pulse generator are electrically connected to certain electrodes within the paddle-like body (hereinafter referred to as the "lead paddle").

Although paddle leads have been implemented successfully, some challenges remain. Fabrication of paddle leads can be complex. Also, the electrical connections within a paddle lead can be subject to failure over time for a variety of reasons.

In addition to the above, the paddle bodies can be rigid or semi-rigid. In SCS, the lead paddle is typically positioned within the epidural space adjacent to the dura of the spinal cord. In some instances, the size of the epidural space and the dimensions of the lead paddle cause the lead paddle to press against the spinal cord. If the compression is substantial, it may cause unwanted consequences, such as a tingling sensation, pain, partial paralysis, or even complete paralysis of the legs.

SUMMARY

In an embodiment, a stimulation lead is provided. The stimulation lead includes an elongated lead body having distal and proximal ends and wire conductors extending therebetween. The stimulation lead also includes a lead paddle having a multi-dimensional array of electrodes positioned along a contact side of the lead paddle. The electrodes are electrically coupled to the wire conductors. The lead paddle includes a paddle body and a conductor organizer disposed within the paddle body. The conductor organizer has multiple channels extending along the lead paddle. The channels receive the wire conductors and retain the wire conductors in a designated arrangement with respect to the lead paddle. The conductor organizer has openings to the channels. The wire conductors extend through the openings and are terminated to the respective electrodes.

In some aspects, the openings are positioned adjacent to respective electrodes of the multi-dimensional array of electrodes.

In some aspects, the conductor organizer includes a plurality of tubes that are connected to one another side-by-side. The tubes define the channels. In other aspects, the tubes are not positioned side-by-side. For example, adjacent tubes may be spaced apart by a gap.

In some aspects, the channels extend parallel to one another for at least a portion of a length of the conductor organizer. In particular aspects, the channels extend parallel to one another for the entire length of the conductor organizer.

In some aspects, the lead paddle includes an inner frame having opposite first and second side surfaces and a flexible layer secured to the first side surface of the inner frame. For example, the flexible layer may be overmolded with respect to the inner frame. The flexible layer defines a portion of the contact side of the lead paddle. The inner frame may be more rigid than the flexible layer. The channels of the conductor organizer extend along and parallel to the second side surface of the inner frame.

In some aspects, the inner frame includes frame windows and the flexible layer includes layer windows that align with the frame windows to form conductor passages. The wire conductors extend through the conductor passages and are mechanically and electrically coupled to the respective electrodes. For example, the wire conductors may be welded or soldered to the electrodes.

In some aspects, the electrodes are arranged in columns that extend longitudinally along the lead paddle. The columns are separated by a spacing. The channels of the conductor organizer may extend along the spacing between the columns of the electrodes.

Optionally, the columns include first and second columns that are adjacent to one another. The channels of the conductor organizer may extend along the spacing between the first and second columns, wherein at least one of the wire conductors that is received by the channels of the conductor organizer is terminated to one of the electrodes of the first column and at least one of the wire conductors that is received by the channels of the conductor organizer is terminated to one of the electrodes of the second column.

In some aspects, the openings of the conductor organizer include at least one side opening and at least one distal opening. The distal opening is at an end of the conductor organizer. The side opening is spaced apart from the at least one distal opening of the conductor organizer.

In some aspects, each of the channels receives only one of the wire conductors. In other aspects, however, the channels may be sized and shaped to receive more than one wire conductor.

In some aspects, the conductor organizer includes a plurality of conductor organizers. Each of the conductor organizers may receive a plurality of the wire conductors.

In an embodiment, a method is provided that includes positioning electrodes along at least one body layer to form a multi-dimensional array and positioning a conductor organizer along the at least one body layer. The conductor organizer has multiple channels extending therethrough. The method also includes inserting wire conductors into the channels of the conductor organizer. The conductor organizer retains the wire conductors in a designated arrangement with respect to the at least one body layer. The conductor organizer has openings to the channels. The wire conductors extend through the openings (e.g., side opening and/or distal openings). The method also includes electrically coupling the wire conductors to respective electrodes.

In some aspects, the at least one body layer is a multi-layered structure that includes conductor passages that align with respective electrodes. The method may also include directing the wire conductors through the conductor passages.

In some aspects, the at least one body layer has a first lateral section and a second lateral section. The method may also include providing a lead body having distal and proximal ends. The lead body also includes first and second windings of the wire conductors. The first winding is wrapped in a first direction along the lead body. The second winding is wrapped in a second direction along the lead body. The method also includes positioning the first and second windings of the wire conductors onto the at least one body layer. The first winding and the second winding are positioned in a splayed configuration such that the first winding extends toward the first lateral section and the second winding extends toward the second lateral section.

In some aspects, the electrodes are arranged in columns. The columns may be separated by a spacing. The channels of the conductor organizer may extend along the spacing between the columns of the electrodes.

In an embodiment, a stimulation lead is provided that includes a lead paddle having a contact side that includes electrodes. The lead paddle has a first lateral section and a second lateral section. The stimulation lead also includes a lead body having a distal and proximal ends. The lead body includes first and second windings of wire conductors. The first winding is wrapped in a first direction along the lead body. The second winding is wrapped in a second direction along the lead body. The first winding and the second winding project from the lead body in a splayed configuration such that the first winding extends toward the first lateral section of the lead paddle and the second winding extends toward the second lateral section of the lead paddle.

In some aspects, a bonding material holds the wire conductors of the first winding side-by-side to form a first conductor layer and a bonding material holds the wire conductors of the second winding side-by-side to form a second conductor layer. The first and second conductor layers project from the leady body in the splayed configuration. Optionally, the bonding material for the first and second conductor layers is at least partially removed after a distance from the lead body.

In some aspects, the lead paddle includes a paddle body and first and second conductor organizers disposed within the paddle body. The first and second conductor organizers have channels extending along the lead paddle. The channels receive the wire conductors and retain the wire conductors in a designated arrangement with respect to the lead paddle.

The first conductor organizer is within the first lateral section, and the second conductor organizer is within the second lateral section.

In some aspects, the lead body has only a single lumen. The first winding of the wire conductors is wrapped about the lumen in a first direction and the second winding of the wire conductors is wrapped about the first winding and the lumen in a second direction.

In an embodiment, a method is provided that includes providing a multi-layered structure having a first lateral section and a second lateral section. The multi-layered structure has electrodes along the multi-layered structure that form a multi-dimensional array. The method also includes providing a lead body having distal and proximal ends. The lead body also includes first and second windings of wire conductors. The first winding is wrapped in a first direction along the lead body, and the second winding is wrapped in a second direction along the lead body. The method also includes positioning the first and second windings of the wire conductors onto the multi-layered structure. The first winding and the second winding are positioned in a splayed configuration such that the first winding extends toward the first lateral section of the multi-layered structure and the second winding extends toward the second lateral section of the multi-layered structure.

In an embodiment, a stimulation lead is provided that includes an elongated lead body having wire conductors extending between distal and proximal ends of the lead body. The stimulation lead also includes a lead paddle coupled to the distal end of the lead body and having a contact side that is configured to face tissue. The contact side has a multi-dimensional array of electrodes that are electrically coupled to the wire conductors. The lead paddle extends lengthwise along a longitudinal axis, wherein the lead paddle has a neutral plane extending therethrough with a neutral longitudinal force envelope (NLFE) surrounding the neutral plane. The lead paddle includes an inner frame having opposite first and second side surfaces. The first side surface faces the contact side. The lead paddle also includes a flexible layer secured to the first side surface of the inner frame and defining a portion of the contact side of the lead paddle. The wire conductors extend along the second side surface of the inner frame and at least a portion of the wire conductors and inner frame are positioned to extend along the NLFE such that, when the lead paddle is flexed transverse to the longitudinal axis by a predetermined amount, the portion of the wire conductors and inner frame within the NLFE experience no more than a predetermined limit of tensile stress or compression stress.

In some aspects, centers of the wire conductors are spaced from the second side surface of the inner frame by a distance that is less than twice a diameter of the wire conductors.

In some aspects, the wire conductors do not cross over one another and the wire conductors do not cross over the electrodes, except for the respective electrodes that the wire conductors are electrically coupled to.

In some aspects, the lead paddle also includes a backing layer. The inner frame is disposed between the flexible layer and the backing layer. The wire conductors extend through the backing layer.

In some aspects, the backing layer includes a back side of the lead paddle that is generally opposite the contact side. The backing layer defines raised portions and recessed portions separated by the raised portions along the back side. The wire conductors extend through the recessed portions.

In some aspects, the flexible layer and the backing layer are shaped to form thin sections of the lead paddle and thick sections of the lead paddle. The thin sections have a thickness of the lead paddle that is less than a thickness of the thick sections. The wire conductors extend through the thin sections.

In some aspects, the inner frame and the flexible layer are a pre-formed multi-layered structure. The backing layer is molded to the pre-formed multi-layered structure.

In some aspects, the inner frame includes frame windows and the flexible layer includes layer windows that align with the frame windows to form conductor passages. The wire conductors extend through the conductor passages and are mechanically and electrically coupled to the electrodes.

In some aspects, the electrodes include projections that extend through the flexible layer and couple to the inner frame. The projections are pierced through the flexible layer.

In some aspects, the inner frame includes grooves or channels that align with and extend parallel to the wire conductors.

In some aspects, the lead paddle includes a conductor organizer that has multiple channels extending through the lead paddle. The channels receive the wire conductors. The conductor organizer is configured to retain the wire conductors in a designated arrangement with respect to the lead paddle. For example, the conductor organizer is configured to retain the wire conductors in a designated arrangement with respect to the electrodes. The conductor organizer extends through the NLFE.

In some aspects, the lead paddle has a first lateral section and a second lateral section. The lead body also includes first and second windings of the wire conductors. The first winding is wrapped in a first direction along the lead body. The second winding is wrapped in a second direction along the lead body. The first winding and the second winding project from the lead body in a splayed configuration such that the first winding extends toward the first lateral section of the lead paddle and the second winding extends toward the second lateral section of the lead paddle.

In an embodiment, a method is provided that includes providing a multi-layered structure having an inner frame and a flexible layer secured to the inner frame. The inner frame is more rigid than the flexible layer. The method also includes positioning electrodes along the flexible layer to form a multi-dimensional array. The electrodes extend through the flexible layer and couple to the inner frame. The method also includes positioning the wire conductors along the second side surface of the inner frame. The method also includes molding a backing layer to the multi-layered structure to form a lead paddle extending lengthwise along a longitudinal axis. The lead paddle has a neutral plane extending therethrough with a neutral longitudinal force envelope (NLFE) surrounding the neutral plane, wherein at least a portion of the wire conductors and inner frame are positioned to extend along the NLFE such that, when the lead paddle is flexed transverse to the longitudinal axis by a predetermined amount, the portion of the wire conductors and inner frame within the NLFE experience no more than a predetermined limit of tensile stress or compression stress.

In some aspects, the multi-layered structure includes conductor passages that align with respective electrodes. The method also includes directing the wire conductors through the conductor passages and positioning the wire conductors adjacent to the respective electrodes. The method also includes mechanically and electrically coupling the wire conductors to the respective electrodes.

In some aspects, the method also includes positioning a conductor organizer along the inner frame of the multi-layered structure. The conductor organizer has respective channels that receive the wire conductors.

In some aspects, the wire conductors do not cross over one another and the wire conductors do not cross over the electrodes, except for the respective electrodes that the wire conductors are terminated to.

In some aspects, the multi-layered structure has a first lateral section and a second lateral section. The method also includes providing a lead body having distal and proximal ends. The lead body also includes first and second windings of the wire conductors. The first winding is wrapped in a first direction along the lead body. The second winding is wrapped in a second direction along the lead body. The method also includes positioning the first and second windings of the wire conductors onto the multi-layered structure. The first winding and the second winding project from the lead body in a splayed configuration such that the first winding extends toward the first lateral section of the multi-layered structure and the second winding extends toward the second lateral section of the multi-layered structure.

In some embodiments, an implantable stimulation lead for stimulation of neural tissue of a patient is provided. The lead comprises: an elongated lead body having distal and proximal ends and wire conductors extending therebetween; and a paddle structure adapted to be implanted adjacent to neural tissue for electrical stimulation, the paddle structure comprising a flexible polymer body, electrodes arranged in a multi-dimensional pattern and positioned along a contact side of the flexible polymer body, and a plurality of sets of microtubes with each microtube having an inner lumen; wherein (1) the electrodes are electrically coupled to the wire conductors of the lead body through wires positioned within the inner lumens of the plurality of sets of microtubes, (2) each set of microtubes are positioned to extend along the paddle structure, and (3) the polymer body of the paddle structure flexes transversely about its longitudinal axis and the plurality of sets of microtubes are arranged generally parallel to the longitudinal axis.

A method of fabricating an implantable stimulation lead for provision of electrical stimulation to tissue of a patient is provided. The method comprises: providing a paddle structure adapted to be implanted adjacent neural tissue for electrical stimulation, the paddle structure comprising a flexible polymer body; providing electrodes arranged in a multi-dimensional pattern and positioned along a contact side of the flexible polymer body; providing a plurality of sets of microtubes with each microtube having an inner lumen on the flexible polymer body; routing a wire through each respective microtube of the plurality of sets of microtubes; and electrically coupling the wires within plurality of sets of microtubes to respective electrodes positioned along a contact side of the flexible polymer body, wherein the polymer body of the paddle structure flexes transversely about its longitudinal axis and the plurality of sets of microtubes are arranged generally parallel to the longitudinal axis.

In some embodiments, a method of fabricating a stimulation lead for electrical stimulation of tissue of a patient is provided. The method comprises: providing a paddle structure adapted to be implanted adjacent neural tissue for electrical stimulation, the paddle structure comprising a flexible polymer body; providing electrodes arranged in a multi-dimensional pattern and positioned along a contact side of the flexible polymer body; providing a plurality of sets of microtubes on the flexible polymer body, each microtube having an inner lumen; providing a lead body comprising a first plurality of conductor wires and a second plurality of conductor wires extending between a proximal and distal end of the lead body; routing a conductor wire through the inner lumen of each respective microtube of the plurality of sets of microtubes, wherein the routing comprising separating a first backing layer for the first plurality of conductor wires and a second backing layer for the second plurality of conductors wires at a distal end of the lead body to couple the first plurality of conductor wires to electrodes on a first side of the paddle structure and to couple the second plurality of conductor wires to electrodes on a second side of the paddle structure; and electrically coupling the conductor wires within plurality of sets of microtubes to respective electrodes positioned along a contact side of the flexible polymer body, wherein the polymer body of the paddle structure flexes transversely about its longitudinal axis and the plurality of sets of microtubes are arranged generally parallel to the longitudinal axis.

In some embodiments, an elongated lead body is provided having distal and proximal ends. The lead body comprises a first plurality of wire conductors and a second plurality of wire conductors extending between the distal and proximal ends, wherein the first plurality of conductor wires are bonded to a first backing layer and the second plurality of conductor wires are bonded to a second backing layer. The lead body comprises a paddle structure adapted to be implanted adjacent to neural tissue for electrical stimulation, the paddle structure comprising a flexible polymer body, electrodes arranged in a multi-dimensional pattern and positioned along a contact side of the flexible polymer body, and a plurality of sets of microtubes with each microtube having an inner lumen. The first and second plurality of conductor wires extend beyond the first backing layer and second backing layer at a distal end of the lead body and are positioned within the inner lumens of the plurality of sets of microtube of the paddle structure. The electrodes are electrically coupled to the first and second plurality of wire conductors, (2) each set of microtubes are positioned to extend along the paddle structure. The polymer body of the paddle structure flexes transversely about its longitudinal axis and the plurality of sets of microtubes are arranged generally parallel to the longitudinal axis.

DETAILED DESCRIPTION

Figure 1:
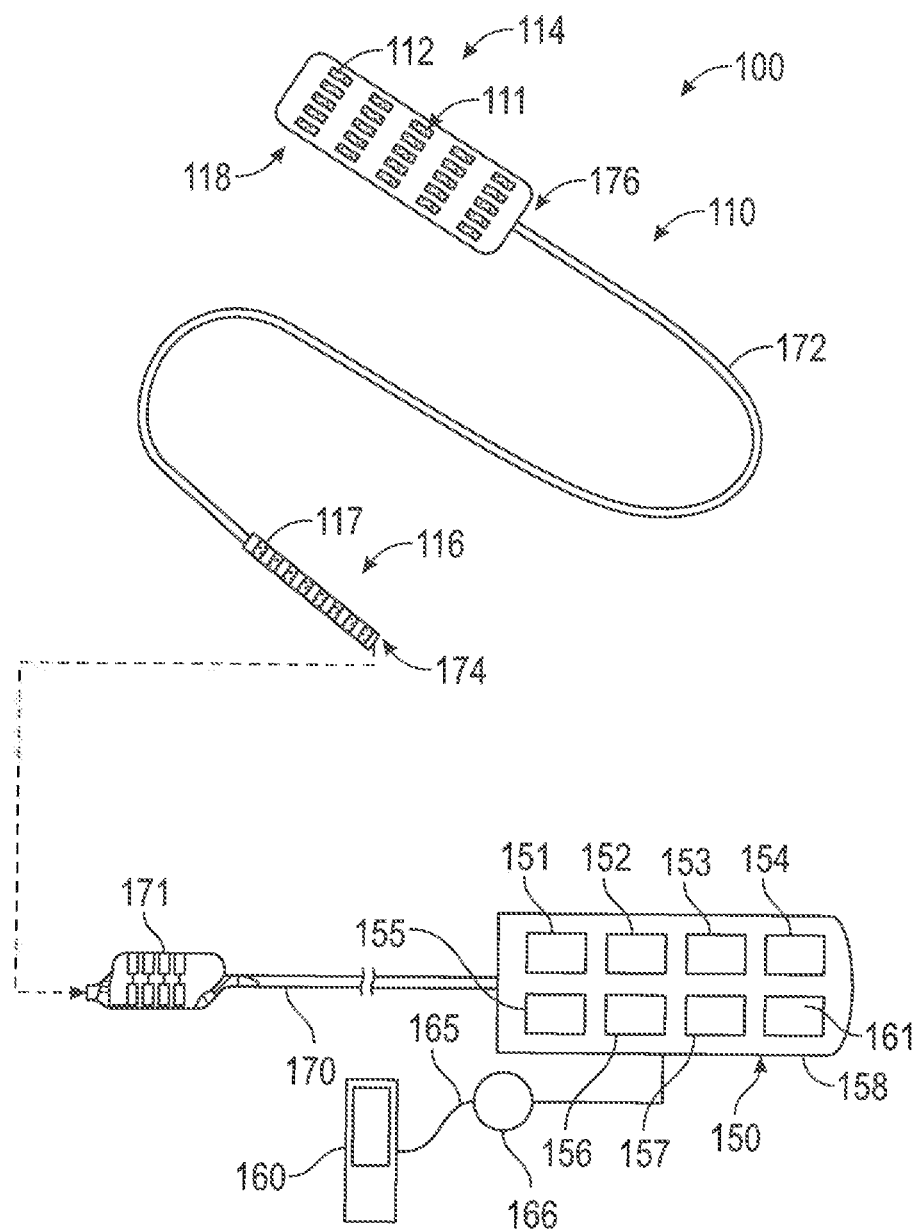
FIG. 1 depicts a schematic block diagram of an embodiment of a stimulation system that includes a paddle lead.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Embodiments set forth herein include systems, neurostimulation leads, paddle bodies, and methods relating to the same that use a multi-dimensional electrode array. The electrodes of the multi-dimensional electrode array are capable of generating electrical pulses and delivering the pulses to nerve tissue to treat a variety of disorders. For example, one or more embodiments may be configured for spinal cord stimulation (SCS). It is contemplated that embodiments may have applications other than pain alleviation.

Paddle bodies set forth herein may be easier to manufacture, may be less time-consuming to manufacture, and/or may be less costly to manufacture. One or more embodiments may include paddle bodies that are thinner and/or more flexible than conventional paddle bodies. As such, the paddle bodies may reduce the likelihood that the nerve tissue will be unduly compressed. Alternatively, or in addition to the above embodiments, at least some embodiments may impede migration of the lead paddle away from its original position with respect to the nerve tissue.

Optionally, embodiments may be configured to reduce the likelihood that the wire conductors will break or otherwise become inoperable for their intended purpose. For instance, embodiments may have wire conductors that are positioned within the lead paddle (or the paddle body) to reduce or minimize an amount of stress that is experienced by the wire conductors when the lead paddle is flexed. To this end, the wire conductors may be positioned along or near a neutral plane of the lead paddle (or the paddle body). A neutral plane is a conceptual plane that is used in engineering design. When a structure is flexed or bent with respect to a relaxed or steady-state position, the neutral plane of the lead paddle separates one region that is in compression and one region that is in tension.

As used herein, a "neutral longitudinal force envelope (NLFE)" is a portion of the lead paddle that surrounds the neutral plane of the lead paddle. When the lead paddle is flexed or bent, the NLFE experiences a compression stress on one side of the neutral plane that is less than the compression stress experienced outside the NLFE. On the other side of the neutral plane, the NLFE experiences a tensile stress that is less than the tensile stress experienced outside the NLFE. The amount of stress (whether tensile or compression) may not exceed an amount of stress that will cause damage or excessive wear to the lead paddle.

For example, when the lead paddle is flexed transverse to a longitudinal axis of the lead paddle by a predetermined amount, the wire conductors and the inner frame within the NLFE may experience no more than a predetermined limit of tensile stress or compression stress. The predetermined limit may be, for example, the value at which the wire conductors will break due to the stress and/or the wire conductors separate from the electrodes due to the stress. The predetermined limit may be a function of an expected number of times at which the lead paddle will be flexed.

The predetermined amount of flexing is an amount that can be experienced by the paddle lead when operating within expected parameters for the intended application of the paddle lead. For example, if the paddle lead is implanted and positioned adjacent to a portion of the spine (e.g., for SCS), the predetermined amount of flexing is a function of how much the portion of the spine is expected to flex during normal usage.

Either or both of the predetermined limit and the predetermined amount may be a function of an expected number of times that the lead paddle is expected to flex. For example, although the wire conductors may not break when the lead paddle is flexed X amount, the wire conductors may break if the lead paddle is flexed X amount a Y number of times. For some applications, it may be expected that the flexing will occur often in a single day. As such, the predetermined limit may be configured to account for material fatigue that may occur. In some embodiments, when the lead paddle is flexed transverse to a longitudinal axis of the lead paddle by at most a predetermined amount, the wire conductors and the inner frame within the NLFE may experience no more than a predetermined limit of tensile stress or compression stress.

As used herein, phrases such as "a plurality of [elements]," when used in the detailed description and claims, does not necessarily include each and every element that a component may have. The component may have other elements that are similar to the plurality of elements in design or function, but not identical. For example, the phrase "a plurality of openings of the conductor organizer [being/having a recited feature]" does not necessarily mean that each and every opening of the conductor organizer has the recited feature. Other openings may not have the recited feature. Accordingly, unless explicitly stated otherwise using the phrase "each and every [element] of the [component]" (e.g., "each and every opening of the conductor organizer [being/having a recited feature]"), the component may include similar elements that do not have the recited feature.

FIG. 1 depicts a schematic block diagram of an embodiment of a stimulation system 100. In particular embodiments, the stimulation system 100 is a neurostimulation (NS) system 100. The stimulation system 100 is configured to generate electrical pulses (e.g., excitation pulses) for application to tissue of a patient according to one embodiment. For example, the stimulation system 100 may be adapted to stimulate spinal cord tissue, dorsal root, dorsal root ganglion, peripheral nerve tissue, deep brain tissue, cortical tissue, cardiac tissue, muscle, digestive tissue, pelvic floor tissue, and/or any other suitable tissue of interest within a patient's body.

The stimulation system 100 includes an implantable pulse generator (IPG) 150 that is adapted to generate electrical pulses for application to tissue of a patient. The IPG 150 typically comprises a metallic housing or can 158 that encloses a controller circuit 151, pulse-generating circuitry 152, a charging coil 153, a battery 154, a communication circuit 155, battery-charging circuitry 156, switching circuitry 157, and/or the like. The communication circuit 155 may represent hardware that is used to transmit and/or receive data along a bi-directional communication link (e.g., with a device controller 160).

The controller circuit 151 is configured to control the operation of the stimulation system 100. The controller circuit 151 may include one or more processors, a central processing unit (CPU), one or more microprocessors, or any other electronic component or logic-based device that is capable of processing input data according to program instructions. Optionally, the controller circuit 151 may include and/or represent one or more hardware circuits or circuitry that include, are connected with, or that both include and are connected with one or more processors, controllers, and/or other hardware logic-based devices. Additionally or alternatively, the controller circuit 151 may execute instructions stored on a tangible and non-transitory computer readable medium (e.g., the memory 161).

The IPG 150 may include a separate or an attached extension component 170. The extension component 170 may be a separate component. For example, the extension component 170 may connect with a "header" portion (not shown) of the IPG 150. If the extension component 170 is integrated with the IPG 150, internal electrical connections may be made through respective conductive components. Within the IPG 150, electrical pulses are generated by the pulse-generating circuitry 152 and are provided to the switching circuitry 157. The switching circuitry 157 connects to outputs of the IPG 150. Electrical connectors (e.g., "Bal-Seal" connectors) within a connector portion 171 of the extension component 170 or within the IPG header may be employed to conduct various stimulation pulses. The stimulation pulses are transmitted to one or more stimulation leads 110. The stimulation leads 110 may be referred to as neurostimulation leads (or NS leads) 110, in particular embodiments, such as those directed toward SCS.

The stimulation lead 110 includes a lead paddle 114 and a terminal segment 116. The lead paddle 114 has a contact side 118 that is configured to face tissue (e.g., nerve tissue) for stimulating the tissue and/or detecting signals from the tissue. The contact side 118 includes a multi-dimensional electrode array 111 of electrodes 112. The terminal segment 116 of the stimulation lead 110 is configured to be inserted within the connector portion 171 or within the IPG header for electrical connection with respective connectors. The pulses originating from the IPG 150 are provided to the one or more stimulation leads 110. The pulses are then conducted through wire conductors of the stimulation lead 110 and applied to the tissue of a patient via the multi-dimensional electrode array 111. Any suitable known or later developed design may be employed for connector portion 171.

The lead paddle 114 of the stimulation lead 110 includes the electrode array 111. For example, in a planar formation on a lead paddle as disclosed in U.S. Provisional Application No. 61/791,288, entitled, "PADDLE LEADS FOR NEUROSTIMULATION AND METHOD OF DELIVERING THE SAME," which is expressly incorporated herein by reference in its entirety. The electrode array 111 includes a plurality of electrodes 112 that are positioned in a predetermined arrangement. Each of the electrodes 112 is separated from other adjacent electrodes 112 by non-conducting portions of the lead paddle 114. The non-conducting portions may include one or more insulative materials and/or biocompatible materials to allow the stimulation lead 110 to be implantable within the patient. Non-limiting examples of such materials include polysulfone (PSU), silicone, silicone-polyurethane (SiPU), polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 112 may be configured to conduct pulses through their exposed, uninsulated surfaces.

In connection to FIG. 1, the stimulation lead 110 may comprise an elongated lead body 172. The lead body 172 extends between a proximal end 174 and a distal end 176 and has wire conductors, such as the wire conductors 380 in FIG. 12, extending between the distal and proximal ends 176, 174. The proximal end 174 may be located adjacent to or include the terminal segment 116 having electrodes 117. For distinguishing different electrodes, the electrodes 112 may be referred to as paddle electrodes 112 and the electrodes 117 may be referred to as terminal electrodes 117.

The lead paddle 114 is coupled to the lead body 172 at the distal end 176. The lead body 172 includes an insulative material and a plurality of wire conductors that extend through the insulative material. The wire conductors electrically couple the paddle electrodes 112 to corresponding terminal electrodes 117 of the stimulation lead 110. The terminal electrodes 117 are adapted to receive electrical pulses from the IPG 150 and the paddle electrodes 112 are adapted to apply the pulses to the stimulation target of the patient. It should be noted that although the stimulation lead 110 is depicted with twenty-five (25) paddle electrodes 112, the stimulation lead 110 may include any suitable number of paddle electrodes 112 (e.g., less than 25, more than 25) as well as terminal electrodes, and wire conductors. The arrangement of electrodes on the lead paddle 114 and the terminal segment 116 may be positioned in a variety of arrangements. For example, the electrodes 112 may be arranged in a grid (as shown in FIG. 1) or in a staggered manner. Some embodiments may have an irregular arrangement.

Although not required for all embodiments, the lead body 172 of the stimulation lead 110 may be fabricated to flex and elongate upon implantation or advancing within the tissue (e.g., subcutaneous tissue, nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body 172 may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse-generating circuitry (e.g., pulse-generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference in its entirety. One or multiple sets of such circuitry may be provided within the IPG 150. Different pulses on different electrodes 112 may be generated using a single set of the pulse-generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various electrodes of one or more stimulation leads 110 as is also known in the art. Various sets of parameters may define the pulse characteristics and pulse timing for the pulses applied to the various electrodes 112 as is known in the art. Although constant excitation pulse-generating circuitry is contemplated for some embodiments, any other suitable type of pulse generating circuitry may be employed such as constant voltage pulse generating circuitry.

A device controller 160 may be implemented to charge/recharge the battery 154 of the IPG 150 (although a separate recharging device could alternatively be employed), to access memory of the IPG 150, and to program the IPG 150 on the pulse specifications while implanted within the patient.

The device controller 160 is configured to receive and/or transmit information with the stimulation system 100, such as the IPG 150. The device controller 160 may include hardware that is used to transmit and/or receive data along a bi-directional communication link. The device controller 160 may include a transceiver, receiver, transceiver and/or the like and associated circuitry (e.g., antennas) for wirelessly communicating (e.g., transmitting and/or receiving) with the stimulation system 100. For example, protocol firmware for transmitting and/or receiving data along the bi-directional communication link may be stored in memory, which is accessed by the device controller 160. The protocol firmware provides the network protocol syntax for the controller circuit 151 to assemble data packets, establish and/or partition data received along the bi-directional communication links, and/or the like. The bi-directional communication link may be a wireless communication (e.g., utilizing radio frequency (RF)) link for exchanging data (e.g., data packets) between the one or more alternative medical imaging systems, the remote server, and/or the like. The bi-directional communication link may be based on a standard communication protocol, such as a customized communication protocol, Bluetooth, and/or the like.

Additionally or alternatively, the device controller 160 may be operably coupled to a "wand" 165. The wand 165 may be electrically connected to a telemetry component 166 (e.g., inductor coil, RF transceiver) at the distal end of wand 165 through respective wires (not shown) allowing bi-directional communication with the IPG 150. For example, the user may initiate communication with the IPG 150 by placing the wand 165 proximate to the IPG 150. Preferably, the placement of the wand 165 allows the telemetry system of the wand 165 to be aligned with the communication circuit 155 of the IPG 150.

Also, the device controller 160 may permit operation of the IPG 150 according to one or more spinal cord stimulation (SCS) programs or therapies to treat the patient. For example, the SCS program corresponds to the SCS delivered and/or executed by the IPG 150. Each SCS program may include one or more sets of stimulation parameters of the pulses including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 may modify its internal parameters in response to the control signals from the device controller 160 to vary the stimulation characteristics of the stimulation pulses transmitted through the stimulation lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 2:
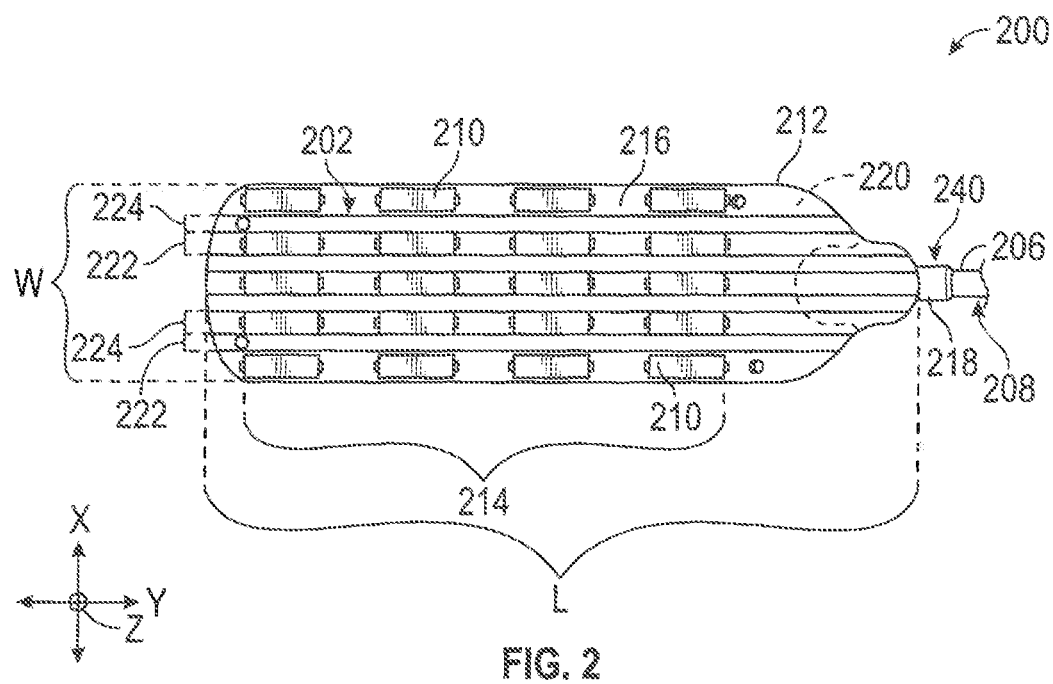
FIG. 2 depicts a contact side of a lead paddle that may form part of a stimulation system, such as the stimulation system of FIG. 1, in accordance with an embodiment.
Figure 3:
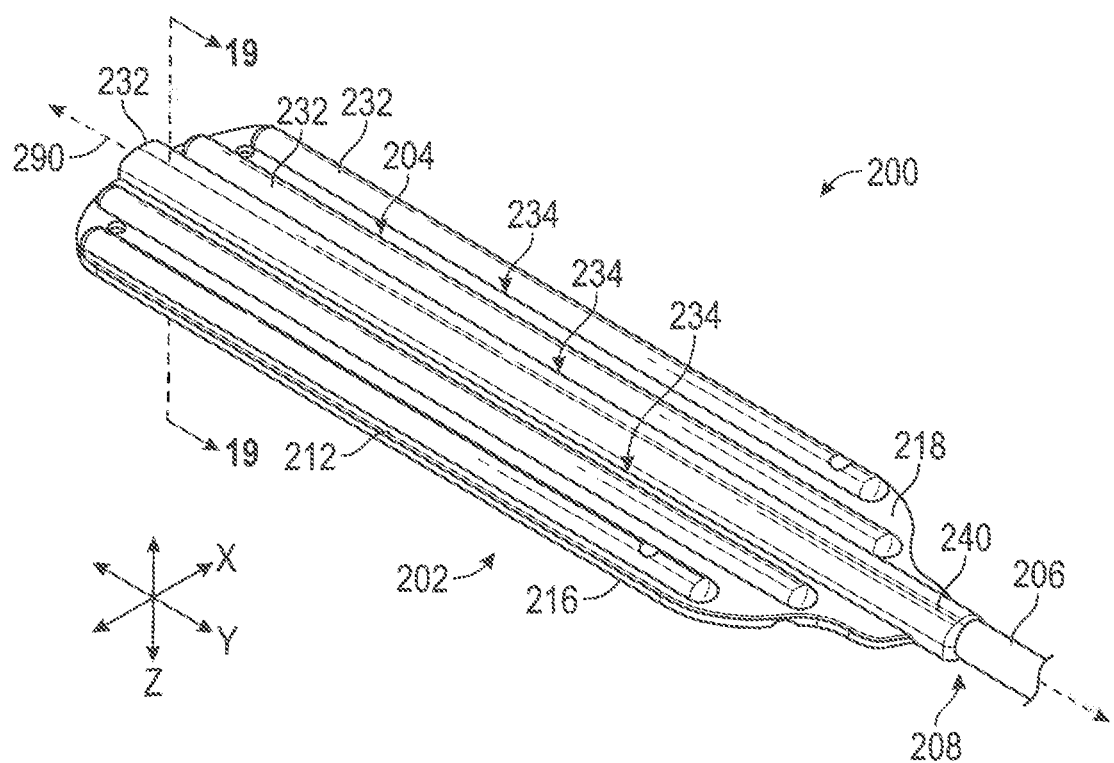
FIG. 3 is a top perspective view of the lead paddle of FIG. 2 in accordance with an embodiment.

FIG. 2 is a plan view of a contact side 202 of a lead paddle 200, and FIG. 3 is a top perspective view of a back side 204 of the lead paddle 200. The lead paddle 200 may form part of an NS system, such as the stimulation system 100 (FIG. 1). For example, the lead paddle 200 may replace the lead paddle 114 (FIG. 1). The lead paddle 200 is coupled to an elongated lead body 206 at a distal end 208 of the lead body 206 to form a stimulation lead, such as the stimulation lead 110 (FIG. 1). Although not shown, the lead body 206 also has a proximal end, such as the proximal end 174 (FIG. 1). Wire conductors extend between the distal end 208 and the proximal end. The lead paddle 200 is oriented with respect to X, Y, and Z axes. As shown in FIG. 3, a longitudinal axis 290 extends through the lead paddle 200 along a length of the lead paddle 200.

The lead paddle 200 includes electrodes 210 (FIG. 2) and paddle body 212. The paddle body 212 includes an insulative material that separates (e.g., electrically isolate) adjacent electrodes 210 from one another. The electrodes 210 are electrically connected to wire conductors 380 (shown in FIG. 12A) that extend through the lead body 206 to, for example, an IPG. The electrodes 210 form a multi-dimensional array 214 of the electrodes 210 along the contact side 202. As used herein, a "multi-dimensional array of electrodes" or "multi-dimensional electrode array" means the electrodes are distributed with respect to one another along at least two dimensions. This is unlike conventional percutaneous leads in which the electrodes are arranged essentially along a single line. For example, the multi-dimensional electrode array 214 has five columns and four rows. A conventional percutaneous lead has one column of electrodes.

In some embodiments, a multi-dimensional array of electrodes may have at least eight (8) electrodes, at least nine (9) electrodes, or at least ten (10) electrodes. In more particular embodiments, the multi-dimensional electrode array has at least 12 electrodes, at least 14 electrodes, or at least 16 electrodes. Yet in more particular embodiments, the multi-dimensional electrode array has at least 20 electrodes. For example, the multi-dimensional electrode array 214 has 20 electrodes.

In FIGS. 2 and 3, the contact side 202 and the multi-dimensional electrode array 214 (FIG. 2) appear substantially two-dimensional (e.g., flat). However, due to the flexibility of the lead paddle 200, the two-dimensional electrode array 214 is permitted to flex when operably positioned. When flexed, the electrodes are distributed with respect to one another along three dimensions (e.g., X, Y, Z).

A paddle body has at least one body layer. In the illustrated embodiment, the paddle body 212 includes three body layers, including a flexible layer 216, a backing layer 218, and an inner frame 220. The body layers are stacked or positioned alongside one another. For example, the flexible layer 216 and the backing layer 218 are positioned on opposite side surfaces of the inner frame 220. The inner frame 220 is illustrated in phantom in FIG. 2. In the illustrated embodiment, each of the body layers extends along substantially an entire width W (FIG. 2) of the paddle body 212 and at least a majority of a length L (FIG. 2). It should be understood that other embodiments may include fewer layers or more layers or that an individual layer may be separated into multiple sections. It should also be understood that other embodiments may have different spatial relationships than those shown in FIGS. 2 and 3.

The flexible layer 216, which may also be referred to as a compliant layer, is secured to the inner frame 220 and defines a portion of the contact side 202. In some embodiments, the inner frame 220 is more rigid (or have a greater stiffness) than the flexible layer 216 and may provide, for example, structural integrity to the paddle body 212 and/or provide a mechanism for attaching the electrodes 210 to the lead paddle 200.

As shown in FIG. 2, the flexible layer 216 is shaped to define raised regions 222 and recessed regions 224 along the contact side 202. The raised regions 222 are separated by the recessed regions 224, and the recessed regions 224 are separated by the raised regions 222. In the illustrated embodiment, the raised regions 222 are elongated ridges that extend parallel to one another. The recessed regions 224 are elongated grooves or open-sided channels that extend parallel to one another. As shown, each of the raised regions 222 and the recessed regions 224 extend parallel to the longitudinal axis 290. In other embodiments, however, the raised regions 222 and/or the recessed regions 224 may not be elongated.

As described herein, the electrodes 210 extend through the raised regions 222 of the flexible layer 216 and couple to the inner frame 220. The electrodes 210 are surrounded by the raised regions 222. The flexible layer 216 may support or facilitate securing the electrodes 210 to the paddle body 212. For example, a raised region 222 may surround a peripheral edge of a corresponding electrode 210. In some embodiments, the electrodes 210 may pierce or puncture the flexible layer 216 and engage the inner frame 220. Alternatively, the electrodes 210 may be overmolded with the flexible layer 216.

The backing layer 218 may define a coupling portion 240 that surrounds the lead body 212. As shown in FIG. 3, the backing layer 218 is shaped to define raised portions 232 and recessed portions 234 along the back side 204. The raised portions 232 are separated by the recessed portions 234, and the recessed portions 234 are separated by the raised portions 232. In the illustrated embodiment, the raised portions 232 are elongated ridges that extend parallel to one another. The recessed portions 234 are elongated grooves or open-sided channels that extend parallel to one another. As shown, each of the raised portions 232 and the recessed portions 234 extend parallel to the longitudinal axis 290.

As described herein, in some embodiments, at least some of the recessed portions 234 of the backing layer 218 and at least some of the recessed regions 224 of the flexible layer 216 align with one another. At least some of the raised portions 232 of the backing layer 218 and at least some of the raised regions 222 of the flexible layer 216 align with one another.

Figure 18:
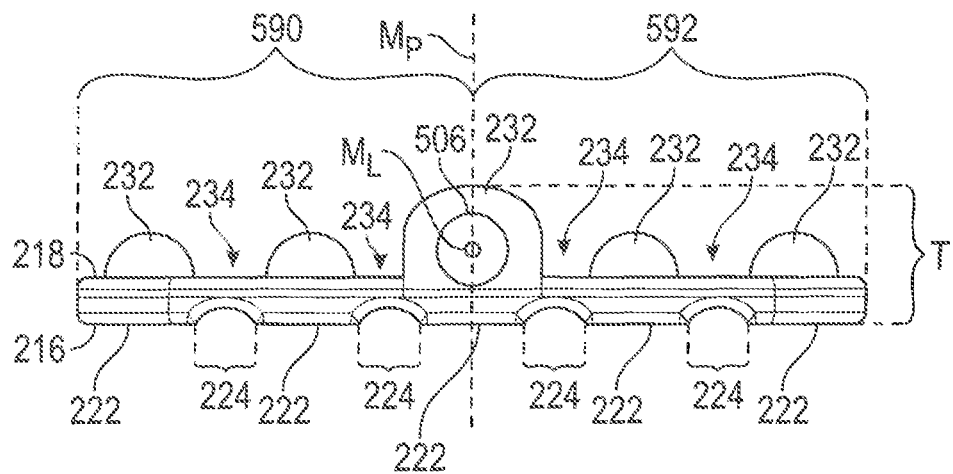
FIG. 18 is an end view of a lead paddle in accordance with an embodiment.

Embodiments may require less space than conventional lead paddles that cover a similar area along the tissue. In other words, embodiments may be thinner than conventional lead paddles. For example, the width W of the lead paddle may be, at most, 12 millimeters. The width W is a maximum distance between opposite lateral edges of the paddle body and is measured when the paddle body is essentially flat. For example, the width W is measured along the X axis when faces of the electrodes of the contact side coincide with a common plane. The lead paddle 200 in FIG. 18 is essentially flat. In certain embodiments, the width W is at most 10 mm. The length L may be, for example, at most 60 mm or at most 55 mm. The length L is a maximum distance between distal and proximal opposite edges of the paddle body and is measured along the longitudinal axis when the paddle body is essentially flat.

A thickness T (FIG. 18) may be, for example, at most 2 mm or at most 1.7 mm. The thickness T is a maximum distance between the contact and back sides of the paddle body and is measured along the Z axis when the paddle body is essentially flat. As described herein, embodiments may have recesses or gaps that reduce a volume of the paddle body. A volume of the lead paddle may be, for example, at most 500 mm$^3$ or at most 450 mm$^3$. The volume of the lead paddle may be determined, for example, by using the measurements of the lead paddle to calculate the volume. The volume of the lead paddle may also be determined by calculating the difference in volume of liquid in a container before and after the lead paddle is placed within the container. Other possible methods may be used. In certain embodiments, the volume of the lead paddle 200 may be, for example, at most 400 mm$^3$ or at most 350 mm$^3$. In particular embodiments, the volume of the lead paddle 200 may be, for example, at most 300 mm$^3$ or at most 275 mm$^3$.

Figure 4:
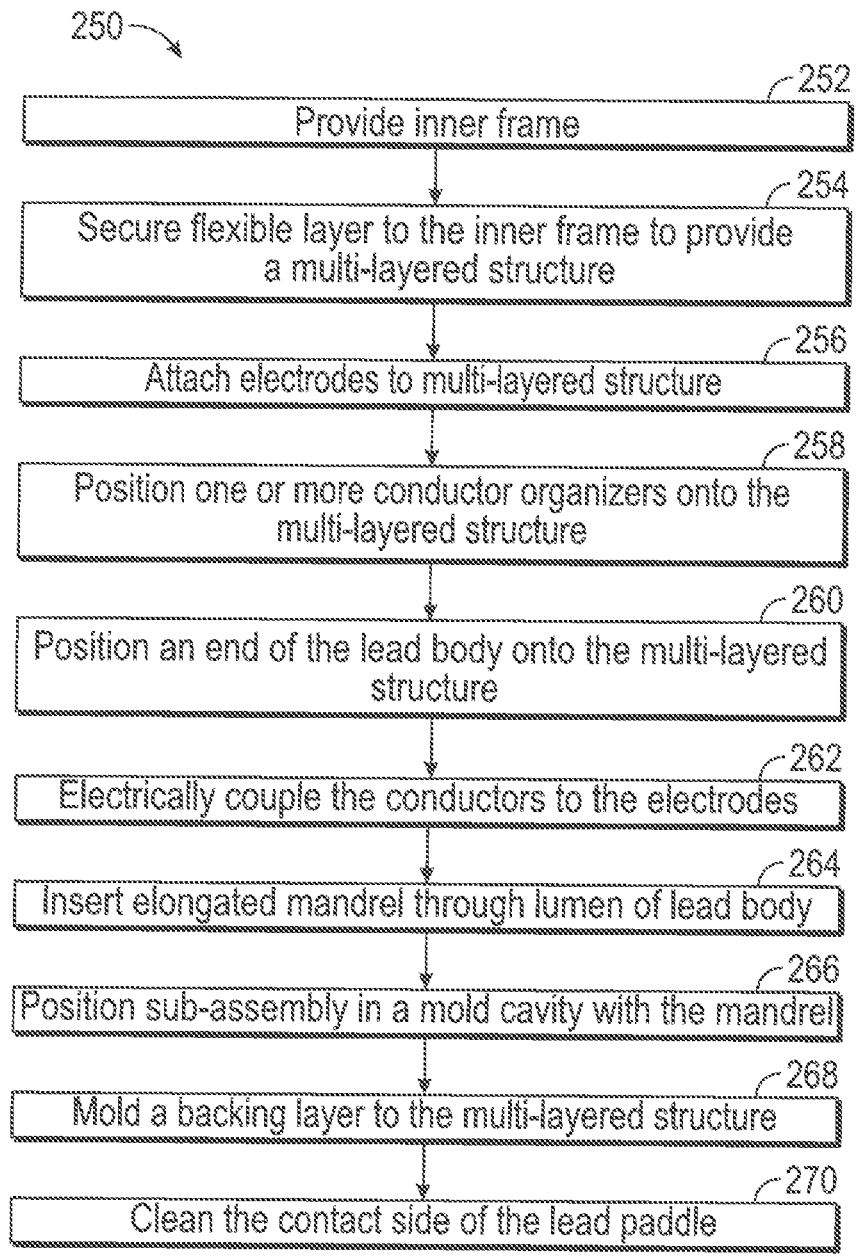
FIG. 4 is a flowchart illustrating a method in accordance with an embodiment.

FIG. 4 is a flowchart illustrating a method 250 in accordance with an embodiment. The method 250 may be, for example, a method of manufacturing a stimulation lead. The method 250, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

Figure 5:
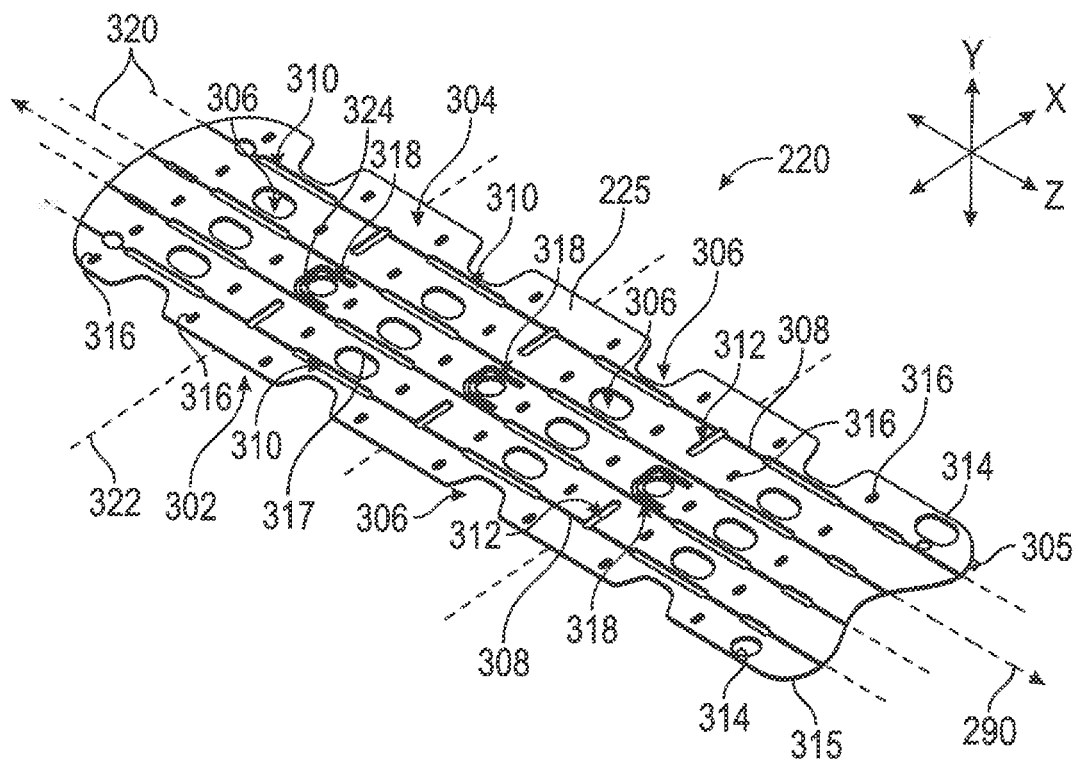
FIG. 5 is a perspective view of an inner frame that may be used to manufacture the lead paddle of FIG. 2 in accordance with an embodiment.

The description of FIGS. 5-16 will refer to the method 250 shown in FIG. 4. The following description of the method 250 and the lead paddle 200 (FIG. 2) illustrates one embodiment. It should be understood that a number of modifications or changes may be made to the lead paddle 200 and/or the method 250. The method 250 includes providing, at 252 (FIG. 4), the inner frame 220 as shown in FIG. 5. The inner frame 220 includes a material sheet 225. The material sheet 225 may be a single piece, as shown in FIG. 5, or maybe two or more separate sections. The material sheet 225 may comprise a thermoplastic material. Non-limiting examples of material that may be used for the inner frame 220 include polysulfone (PSU), polyether ether ketone (PEEK), polyurethane, SiPU, or a glass fiber reinforced polymer.

The inner frame 220 has a first side surface 302, a second side surface 304, and a thickness 305 extending therebetween. In the illustrated embodiment, the thickness 305 is essentially uniform, but other embodiments may utilize inner frames 220 that have portions with different thicknesses. The thickness 305 may be, for example, at most 0.200 mm (0.008 inches (in)) or, more particularly, at most 0.150 mm (0.006 in). In particular embodiments, the thickness may be at most 0.130 mm (0.005 in). As more advanced polymers are developed, it may be possible to use thinner inner frames. Although some embodiments may utilize inner frames with relatively small thicknesses, larger thicknesses may be used. For example, in other embodiments, the thickness 305 is greater than 0.200 mm or greater than 0.500 mm.

The inner frame 220 has an outer frame edge 315. The outer frame edge 315 defines a profile or perimeter of the inner frame 220. The inner frame 220 may be patterned (e.g., laser cut, etched, stamped) to include designated features, such as grooves or openings. For example, the inner frame 220 includes frame windows 306, frame grooves 308, longitudinal thru-channels 310, lateral thru-channels 312, alignment openings 314, and coupling openings 316. The openings are defined by edges, such as the outer frame edge 315 or an inner frame edge 317. The designated features may have one or more functions. For example, the frame windows 306 may be sized and shaped to allow wire conductors 380 (FIG. 12A) to be positioned adjacent to non-contact faces 345 (FIG. 8B) of the electrodes 210 (FIG. 2).

The frame grooves 308 and the longitudinal thru-channels 310 extend parallel to the longitudinal axis 290. The frame grooves 308 extend partially into the thickness 305 of the inner frame 220. The longitudinal thru-channels 310 extend entirely through the thickness 305. As shown, a plurality of the frame grooves 308 and a plurality of the longitudinal thru-channels 310 are aligned with one another in an alternating manner. Aligned frame grooves 308 and longitudinal thru-channels 310 may collectively form a corresponding fold line 320. In FIG. 5, the inner frame 220 includes four fold lines 320, but may include fewer or more fold lines in other embodiments. The fold lines 320 reduce a lateral stiffness of the paddle body 212 (FIG. 2) and permit the paddle body 212 to fold or flex about the fold lines 320.

Optionally, a fold line may include only a single frame groove or multiple frame grooves without a longitudinal thru-channel. In other embodiments, a fold line may include only a single longitudinal thru-channel or multiple longitudinal thru-channels without a frame groove. The longitudinal thru-channel may extend partially along the length L or entirely along the length L. For embodiments in which the longitudinal thru-channel extends along the entire length L, the inner frame 220 may include multiple discrete sections.

The lateral thru-channels 312 extend entirely through the thickness 305. The lateral thru-channels 312 extend parallel to the X axis. Similar to the longitudinal thru-channels 310, the lateral thru-channels 312 may align with other lateral thru-channels 312. The aligned lateral thru-channels 312 may form a fold line 322 that reduces a longitudinal stiffness of the paddle body 212 and permits the paddle body 212 to fold or flex about the fold line 322. The inner frame 220 includes three fold lines 322 in FIG. 5, but may include fewer or more fold lines in other embodiments.

Optionally, the inner frame 220 includes inner thru-channels 319. The inner thru-channels 319 may be shaped to provide tab sections 324. The inner thru-channels 319 and the tab sections 324 may also reduce a longitudinal stiffness of the paddle body 212.

The coupling openings 316 are sized and shaped to receive portions of the electrodes 210. For example, the electrodes 210 (FIG. 2) may include one or more projections 344, 346 (shown in FIG. 8A) that extend through the coupling openings 316 and are deformed to grip the inner frame 220. The alignment openings 314 are configured to receive posts or other projections of a molding apparatus so that the inner frame 220 may be properly positioned before a molding process.

Optionally, the openings and thru-channels may be located to allow polymer or other suitable material (e.g., silicone) to flow during a mold process. For example, the longitudinal thru-channels 310, the lateral thru-channels 312, and other openings may permit the backing layer 218 to flow partially therethrough. After the backing layer 218 has cured or solidified, the backing layer 218 may provide a rubber-band like effect that mechanically retains the inner frame 220. As such, the openings may add to the flexibility of the paddle lead 200 and also reduce the likelihood that the different layers of the paddle body 212 will separate.

The method 250 may also include securing, at 254, the flexible layer 216 (FIG. 6) to the inner frame 220. For example, the inner frame 220 may be positioned within a cavity of a molding apparatus (not shown). A material, which may be a mixture of two or more materials, may be injected into the cavity. In some embodiments, the material may be liquid silicone rubber (LSR), but other materials may be suitable. Through pressure, heat, and/or a catalyst, the material is permitted to solidify into the flexible layer 216. The flexible layer 216 may be referred to as an overmold layer as the material may be permitted to flow into channels, openings, or other available space and effectively surround a portion of the inner frame 220. For example, in the illustrated embodiment, the flexible layer 216 extends around the outer frame edge 315. The backing layer 218 may also extend around the outer frame edge 315 and interface with the flexible layer 216. In such embodiments, the inner frame 220 is encased within the paddle body 212 and material of the backing layer 218 and/or material of the flexible layer 216 exists between the outer frame edge 315 and an exterior of the paddle body 212.

Figure 6:
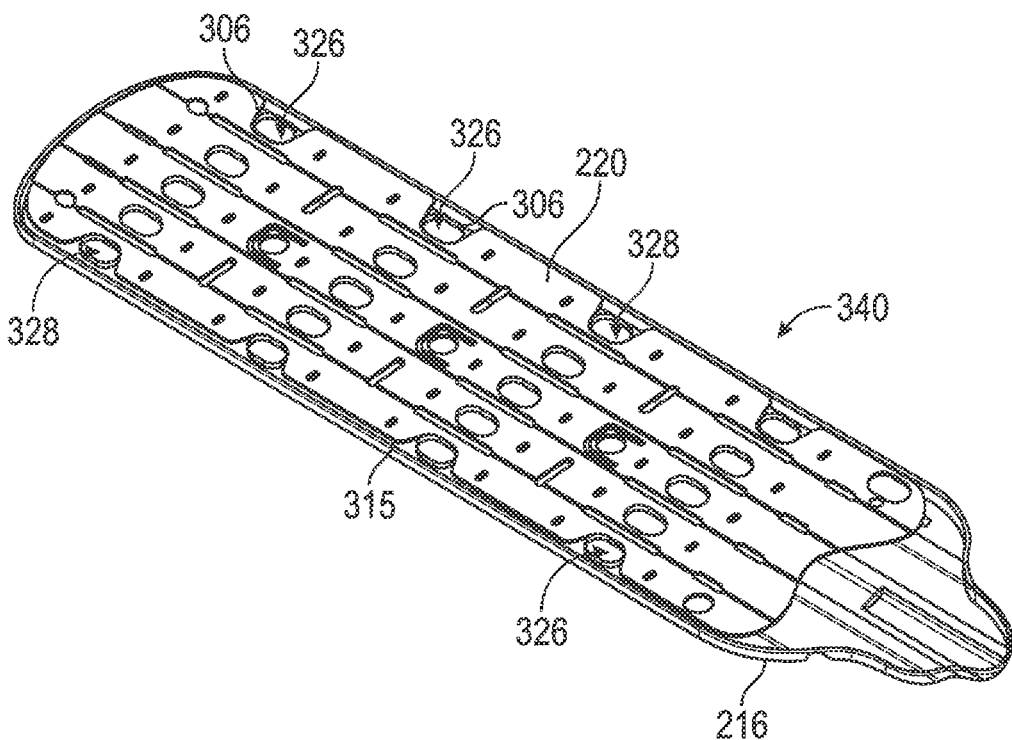
FIG. 6 illustrates a multi-layered structure having the inner frame and a flexible layer secured to the inner frame in accordance with an embodiment.

When secured to one another as shown in FIG. 6, the flexible layer 216 and the inner frame 220 may be referred to as a multi-layered or composite structure 340. In some embodiments, the multi-layered structure 340 is made prior to adding subsequent elements (e.g., backing layer). In such instances, the multi-layered structure 340 may be referred to as a pre-formed structure or, for instances in which the flexible layer 216 is molded, a pre-molded multi-layered structure 340.

As shown in FIG. 6, the flexible layer 216 may include layer windows 326. In some embodiments, the layer windows 326 are defined during the molding process at 254. In other embodiments, the layer windows 326 may be formed subsequently (e.g., through stamping). The flexible layer 216 may also be molded to include the raised regions 222 (FIG. 2) and the recessed regions 224 (FIG. 2). Alternatively, the raised regions 222 and the recessed regions 224 may be formed subsequently by removing material from the flexible layer 216. For instance, after the flexible layer is made, material from the flexible layer may be removed to form recessed regions and, consequently, raised regions.

The layer windows 326 may align with the frame windows 306 to form conductor passages 328. The conductor passages 328 are sized and shaped to permit the wire conductors 380 (FIG. 12A) to extend therethrough so that the wire conductors may be mechanically and electrically coupled to the respective electrodes 210.

Figure 7:
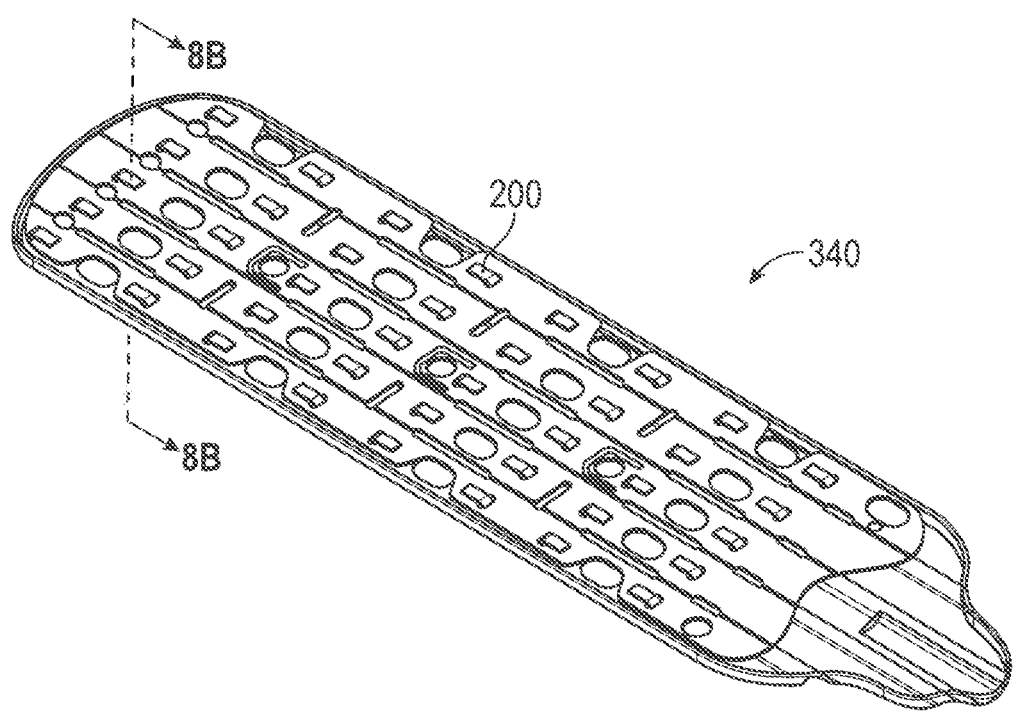
FIG. 7 is a perspective view of the multi-layered structure having electrodes coupled thereto in accordance with an embodiment.
Figure 8A:
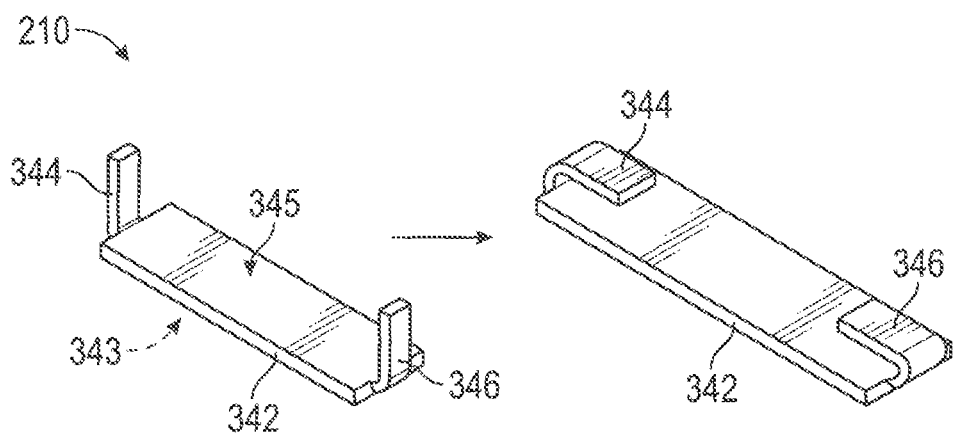
FIG. 8A illustrates how a single electrode may be shaped to couple to the multi-layered structure in accordance with an embodiment.
Figure 8B:
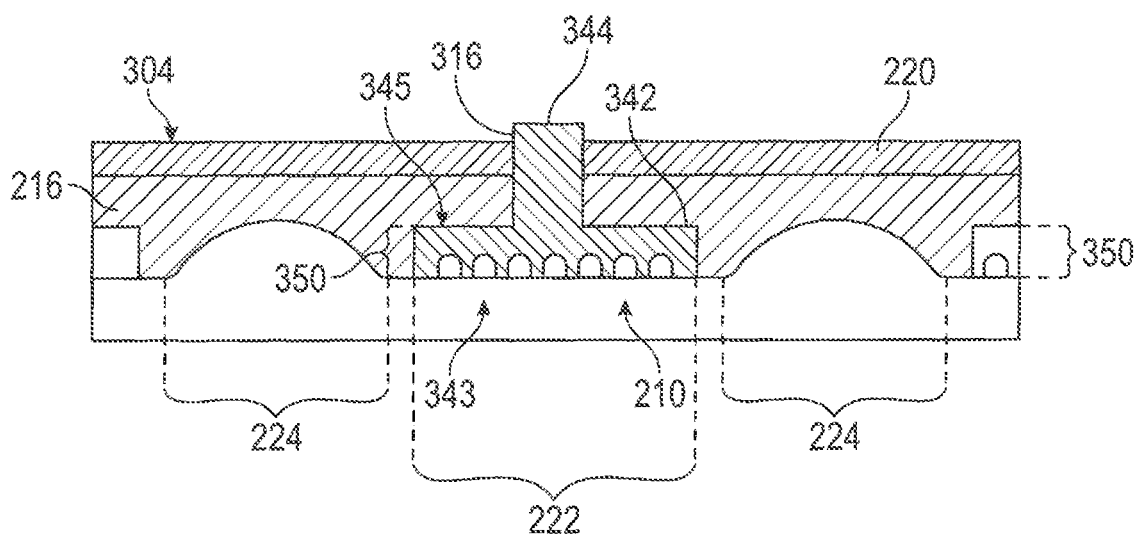
FIG. 8B is a cross-section of the multi-layered structure of FIG. 7 taken along lines 8B-8B.

FIG. 7 is a perspective view of the multi-layered structure (or multi-layered structure) 340. FIG. 8A is an isolated view of a single electrode 210, and FIG. 8B is a cross-section of the multi-layered structure 340 in FIG. 7 taken along lines 8B-8B. At 256 of the method 250 (FIG. 4), the electrodes 210 may be attached to the multi-layered structure 340. The electrodes 210 may be stamped and formed. As shown in FIGS. 8A and 8B, the electrode 210 includes a contact segment 342 and projections 344, 346 (FIG. 8A). The contact segment 342 has a contact face 343 that is configured to interface with the tissue. The projections 344, 346 are tabs in the illustrated embodiment, but may take other shapes in other embodiments. As shown in FIG. 8A, the projections 344, 346 are deformed in a manner that is similar to stapling.

FIG. 8B also shows the raised regions 222 and the recessed regions 224. The electrodes 210 extend through corresponding raised regions 222 of the flexible layer 216 and couple to the inner frame 220. As shown, the projection 344 grips the inner frame 220 and holds the electrode 210 against the flexible layer 216. The electrodes 210 may be secured to the multi-layered structure 340 through a coupling process, which may be similar to a stapling process in some embodiments. For example, the projections 344, 346 may pierce or puncture the flexible layer 216 and extend through the coupling openings 316. The material of the flexible layer 216 is displaced during the piercing or puncturing process. After or as the projections 344, 346 advance through the coupling openings 316, the projections 344, 346 (FIG. 8A) are deformed to be pressed against the second side surface 304 of the inner frame 220.

In some embodiments, the flexible layer 216 may include seating spaces 350 that are sized and shaped to receive the contact segments 342. The seating spaces 350 may be shaped with the layer windows 326 (FIG. 6). In other embodiments, the flexible layer 216 is not shaped to include seating spaces. Instead, the stapling process in which the electrodes 210 are secured to the multi-layered structure 340 may partially form the seating spaces by displacing material of the flexible layer 216. Alternatively, the seating spaces may not exist after the stapling process. As shown in FIG. 8B, the contact face 343 of the contact segment 342 may be pitted to include micro-dimples. The electrodes 210 may comprise a suitable conductive material. For example, the electrodes 210 may comprise platinum and iridium.

In FIG. 8, the electrodes 210 are surrounded by the corresponding raised regions 222. Specifically, the material of the flexible layer 216 engages (e.g., presses against) and surrounds the projections 344, 346 such that the projections 344, 346 are held in fixed positions. The material of the flexible layer 216 also exists between the non-contact face 345 of the contact segment 342 and the first side surface 302 of the inner frame 220. The material of the flexible layer 216 may be compressed between the inner frame 220 and the contact segment 342. Accordingly, the flexible layer 216 and the inner frame 220 hold the electrodes 210 in substantially fixed positions.

Figure 9:
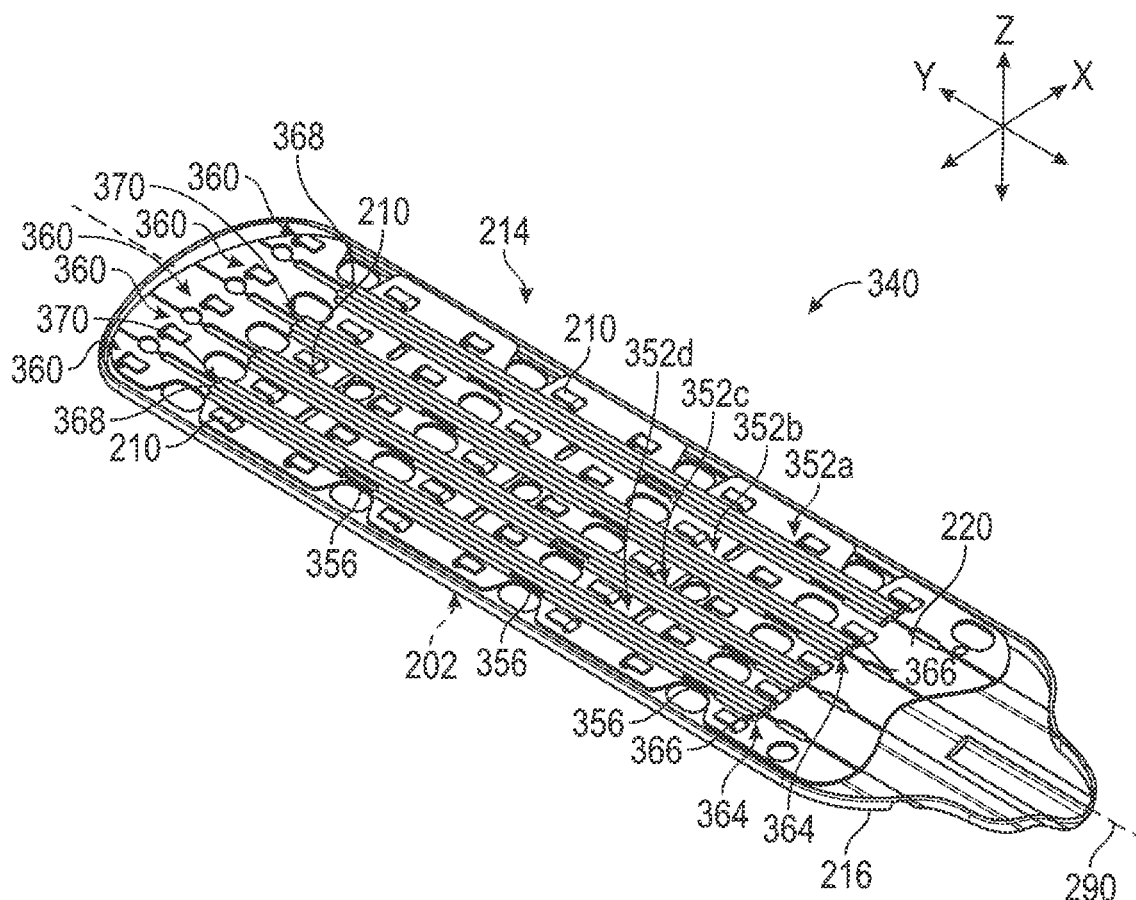
FIG. 9 is a perspective view of the multi-layered structure having conductor organizers positioned thereon in accordance with an embodiment.
Figure 10:
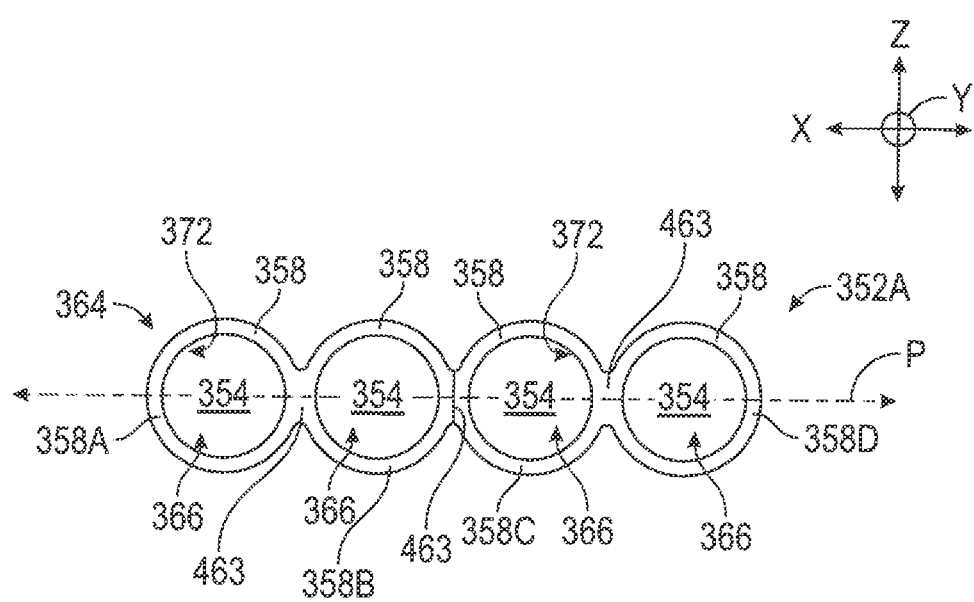
FIG. 10 is an end view of an exemplary conductor organizer in accordance with an embodiment.

FIG. 9 is a perspective view of the multi-layered structure 340 having conductor organizers 352A-352D positioned thereon, and FIG. 10 is an end view of a first organizer end 364 of the conductor organizer 352A. The conductor organizers 352A-352D include organizer channels 354 (FIG. 10) and are configured to facilitate positioning the wire conductors 380 (FIG. 12A) during assembly. For example, the conductor organizers 352A-352D may route (or direct) the wire conductors 380 to designated positions along the paddle body 212 (FIG. 1) as the wire conductors 380 are moved through the conductor organizers 352A-352D. The conductor organizers 352A-352D are also configured to retain the wire conductors 380 therein while other elements (e.g., other wire conductors) are being moved or assembled. Each of the conductor organizers 352A-352D extends between the first organizer end 364 and a second organizer end 370.

At 258 of the method 250 (FIG. 4), one or more conductor organizers may be positioned along the inner frame (or the multi-layered structure). With respect to FIG. 9, the contact side 202 and the conductor organizers 352A-352D are positioned on opposite sides of the inner frame 220. For example, the conductor organizer 352A has a plurality of the organizer channels 354 (shown in FIG. 10) that are sized and shaped to retain the wire conductors 380. In the description and claims, the organizer channels 354 may be referred to as "organizer channels" or simply as "channels." Although a more detailed description is provided for the conductor organizer 352A, the other conductor organizers 352B-352D may have similar features.

In certain embodiments, the conductor organizers are discrete elements such that the conductor organizers are separate and distinct elements with respect to the body layers of the paddle body as the paddle body is assembled. For example, with respect to the paddle body 212 (FIG. 2), the conductor organizers 352A-352D may be separate and distinct elements with respect to the flexible layer 216, the backing layer 218 (FIG. 3), and/or the inner frame 220 as the paddle body 212 is assembled. The conductor organizers 352A-352D may or may not comprise the same material as one of the body layers. For instance, in some embodiments, the conductor organizer may comprise the same material as the inner frame. In such instances, however, the conductor organizers and the inner frame may be separate parts.

In other embodiments, however, the inner frame may also function as a conductor organizer. For instance, the inner frame may provide structural integrity to the paddle body and/or provide a mechanism for attaching the electrodes to the lead paddle, but also provide a mechanism for routing and retaining the wire conductors. As an example, the inner frame may include tabs that extend away from the planar body of the inner frame. The tabs may be used to generally retain the wire conductors in position prior to terminating the wire conductors to the electrodes and/or molding the backing layer to the multi-layered structure.

In some embodiments, however, the conductor organizers comprise a different material with respect to the body layer(s). For example, the conductor organizers 352A-352D may comprise a suitable thermoplastic or polymer material, such as polycarbonate polyurethane (PCU).

In the illustrated embodiment, the conductor organizers 352A-352D are substantially planar structures that each extend along a linear path that is parallel to the longitudinal axis 290 (FIG. 3). In other embodiments, the conductor organizers 352A-352D may follow paths that are not linear.

Accordingly, the conductor organizers 352A-352D are configured to provide multiple channels 354. The channels 354 are configured to receive the wire conductors 380 (FIG. 12A) and retain the wire conductors 380 in a designated arrangement with respect to the lead paddle 200 (FIG. 1) or the paddle body 212 (FIG. 1). Specifically, interior surfaces 372 that define the channels 354 are configured to retain the wire conductors in a designated arrangement with respect to the lead paddle 200.

Figure 12A:
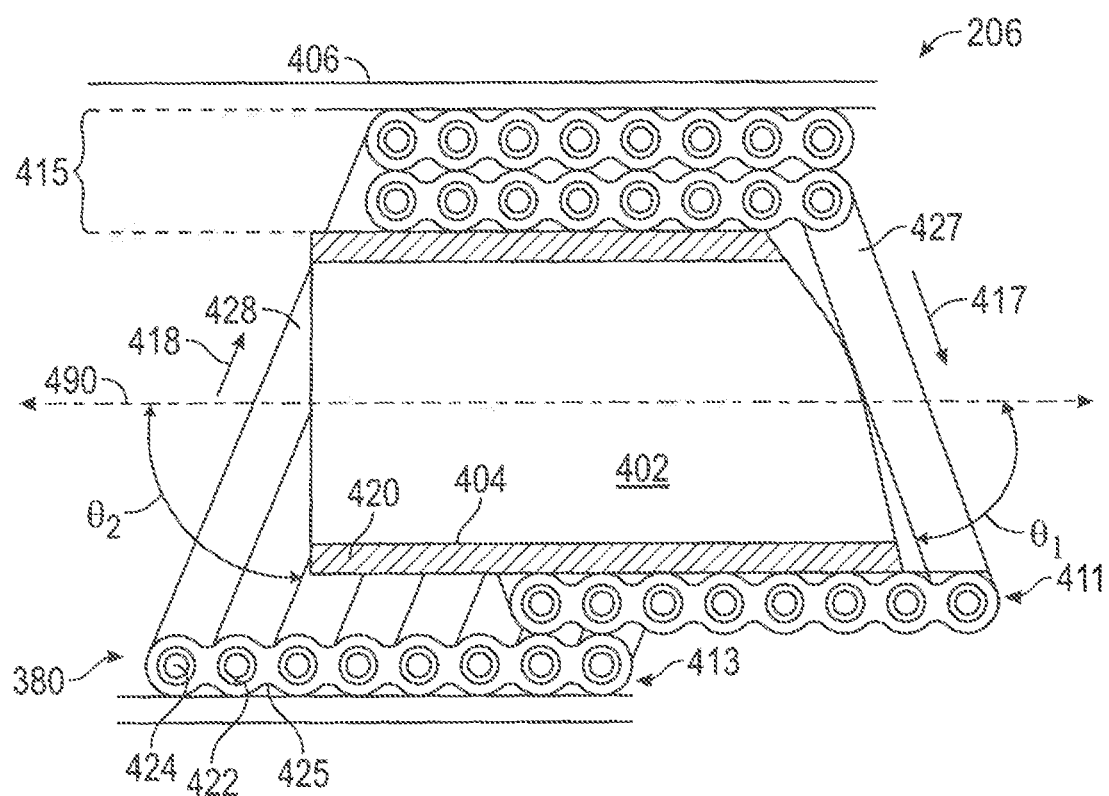
FIG. 12A is a cross-section of a lead body in accordance with an embodiment.

As shown in FIG. 9, each of the conductor organizers 352A-352D has proximal openings 366, distal openings 368, and at least one side opening 356. The proximal openings 366 may be referred to as inlet openings 366 as the wire conductors may be initially inserted through the openings 366. The distal openings 368 and the side openings 356 may be referred to as outlet openings as the wire conductors may exit the channels 354 through the outlet openings. The proximal openings 366 are also shown in FIG. 10. The proximal openings 366 are openings to respective channels 354 and are sized and shaped to receive one or more wire conductors 380 (FIG. 12A). The distal openings 368 are associated with the channels 354 and are sized and shaped to permit the wire conductors 380 to exit the channel 354. However, at least some of the distal openings 368 may not have a wire conductor extending therethrough. Each of the channels 354 has at least one proximal opening 366 and at least one side opening 356 and/or at least one distal opening 368. As shown, each of the side openings 356 is spaced apart from the distal openings 368 of the same conductor organizer and is positioned along a side of the corresponding conductor organizer. Each side opening 356 is accessed through the side of the corresponding conductor organizer. The side openings 356 open in one of two directions along the X axis. The proximal and distal openings 366, 368 open in opposite directions along the Y axis.

With respect to FIG. 9, the side openings 356 are sized and shaped to permit the wire conductors 380 to extend through the side openings 356 and be terminated to the respective electrodes 210. Each channel 354 may be associated with zero side openings, one side opening, or more than one side opening (e.g., two or three side openings).

In the illustrated embodiment, each of the conductor organizers 352 includes a plurality of tubes 358. The tubes 358 are sized and shaped to receive only a single wire conductor 380 (FIG. 12A). In other embodiments, however, the tubes may be sized and shaped to receive more than one wire conductor (e.g., two, three, or more). As shown, the tubes 358 are connected side-by-side and extend parallel to one another. The channels 354 extend parallel to one another for at least a portion of a length of the conductor organizer 352. In the illustrated embodiment, the channels 354 extend parallel to one another for an entire length of the conductor organizer 352. Optionally, the tubes may not be parallel and may take different paths.

In certain embodiments, the tubes 358 and/or the channels 354 are capable of being essentially coplanar when the lead paddle 200 is flat. For example, a plane P intersects each of the four channels 354 when the lead paddle 200 (FIG. 1) is flat. The conductor organizers 352A-352D are essentially two-dimensional structures and extend parallel to the X and Y axes. However, the conductor organizers 352A-352D may permit flexing or bending during the lifetime operation of the lead paddle 200. In other embodiments, the conductor organizer may have a more three-dimensional structure such that the tubes and/or channels may shift along the Z-axis.

Each of the conductor organizers 352A-352D may be configured to receive a plurality of the wire conductors 380. As shown in FIG. 9, the conductor organizers 352A-352D may be positioned between series of electrodes 210. For example, the multi-dimensional array 214 includes columns 360 of the electrodes 210. The columns 360 extend longitudinally along the lead paddle 200 or parallel to the longitudinal axis 290. As such, the channels 354 of each of the conductor organizers 352A-352D are disposed between the electrodes 210 of adjacent columns 360 or extend parallel to and along a spacing that exists between the adjacent columns 360. The channels 354 of each conductor organizer 352 are disposed between the projections 344, 346 (in FIG. 9). In some embodiments, the wire conductors 380 (FIG. 12A) are positioned to extend between adjacent columns 360 without crossing over an electrode 210.

The tubes 358 are interconnected by shared walls 463. Tubes 358A and 358D may be referred to as outer tubes, and the channels 354 of the tubes 358A, 358D may be referred to as outer channels. Tubes 358B and 358D may be referred to as inner tubes and the channels 354 of the tubes 358B, 358C may be referred to as inner channels. If a fifth tube existed, the middle tube may be referred to as the center tube having a center channel. In alternative embodiments, the tubes 358 may be separated such that a gap exists between adjacent tubes 358. In such embodiments, the conductor organizers may include bridges that extend laterally across the conductor organizers and joins each of the tubes.

Figure 11:
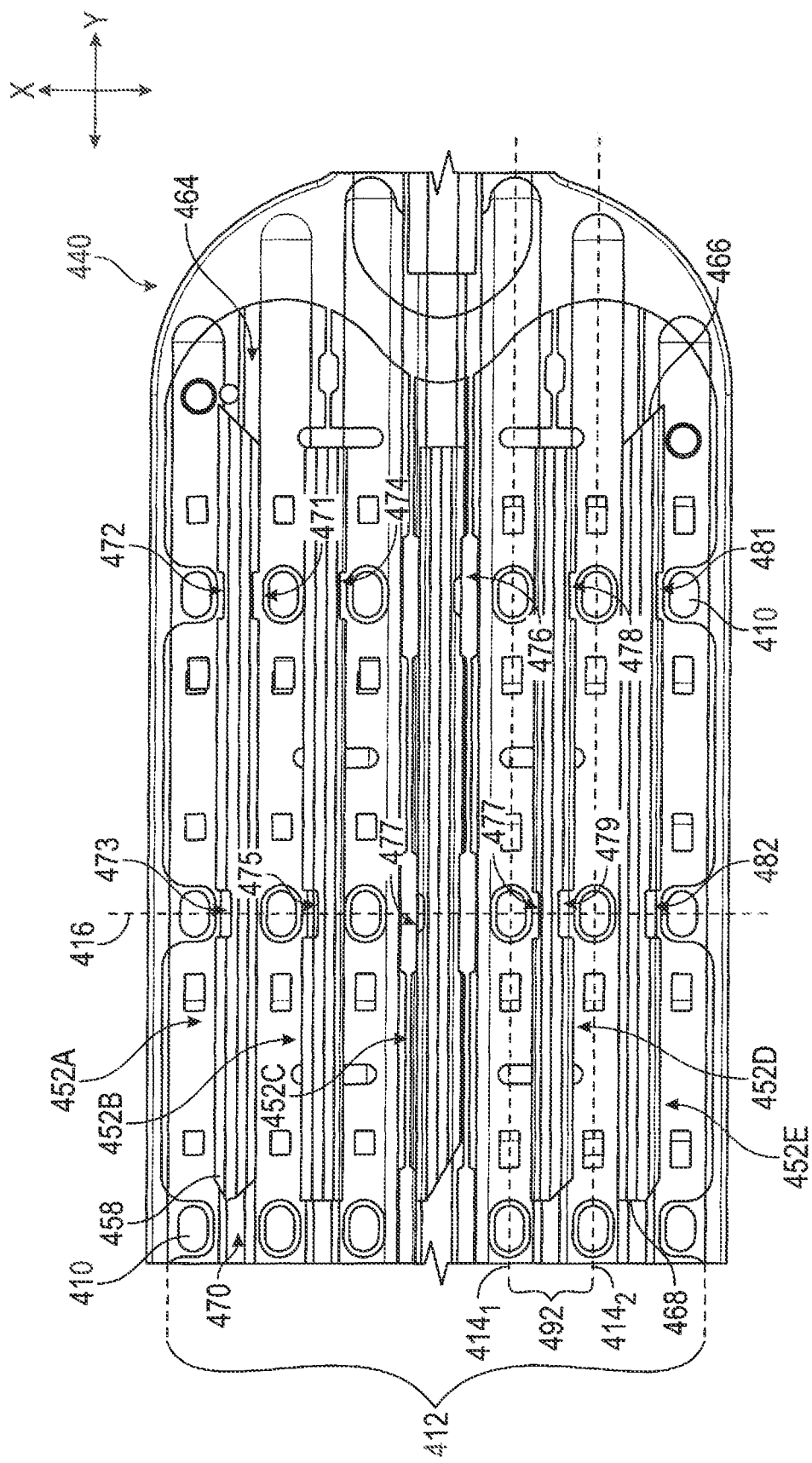
FIG. 11 is a plan view of a multi-layered structure in accordance with another embodiment that includes conductor organizers positioned thereon.

FIG. 11 is a plan view of a portion of a multi-layered structure 440 in accordance with another embodiment that includes conductor organizers 452A-452E positioned thereon. The multi-layered structure 440 will form part of a lead paddle (not shown) that includes eighteen (18) electrodes 410. The electrodes 410 form a multi-dimensional array 412 having columns 414 and rows 416. The columns 414 extend lengthwise along the Y axis, and the rows extend lengthwise along the X axis. Although the multi-dimensional array 412 is shown as a grid-type array, it should be understood that the electrodes 410 may have other positions with respect to one another. For instance, the electrodes 410 may be staggered or have an irregular arrangement (e.g., one portion of the array 412 may have a greater density of electrodes than another portion).

The conductor organizers 452A-452E are configured to retain the wire conductors, such as the wire conductors 380 (FIG. 12A), in a designated arrangement with respect to the lead paddle. Each of the conductor organizers 452A-452E include first and second organizer ends 464, 470 and plurality of interconnected tubes 458 that are coupled side-by-side. Each of the tubes 458 defines a channel in which the channels of the corresponding conductor organizer are essentially coplanar when the lead paddle is flat. For example, a plane extending parallel to the X and Y axes may intersect each of the tubes 458 or each of the channels that are defined by the tubes 458.

The channels (or the tubes 458) of the conductor organizers 452A-452E are disposed between the electrodes 410 of adjacent columns 414 or extend parallel to and along a spacing 492 that exists between the adjacent columns 414. The spacing 492 is a region of the paddle body that exists between the electrodes 410. The spacing 492 may include portions of the paddle body and is not required to be empty space. In alternative embodiments, one or more of the conductor organizers may extend over a column or row of the multi-dimensional array. In such instances, the side openings may open directly above a respective electrode.

In the illustrated embodiment, each of the conductor organizers 452A-452E also includes proximal openings 466 and distal openings 468. The conductor organizers 452A-452E also include side openings. Reference numerals 471-481 more particularly identify the side openings. As shown in FIG. 11, the side openings of the conductor organizers 452A-452E are arranged such that the side openings are positioned adjacent to respective electrodes 410 of the multi-dimensional array 412. For instance, the conductor organizer 452A includes a left-side opening 471 having a first depth, a right-side opening 472 having the first depth that is opposite the left-side opening 471, and a right-side opening 473 having a second depth that is greater than the first depth. The depths are measured along the X axis. Openings with the first depth provide an exit point for wire conductors extending through an outer channel of the conductor organizer. Openings with the second depth provide an exit point for wire conductors extending through an inner channel of the conductor organizer.

Furthermore, the conductor organizer 452B includes a left-side opening 474 having a first depth and a right-side opening 475 having the first depth. The conductor organizer 452C includes a left-side opening 476 having a first depth and a right-side opening 477 having the first depth. The conductor organizer 452D includes a left-side opening 478 having a first depth, a left-side opening 479 having the second depth, and a right-side opening 480 having the first depth. The conductor organizer 452E includes a left-side opening 481 having a first depth and a left-side opening 482 having the second depth.

During assembly the conductor organizers 452A-452E may enable routing and retaining the wire conductors in a manner that is more cost-efficient and/or less time-consuming. For example, the conductor organizer 452D is positioned between adjacent first and second columns $414_1$, $414_2$ of the electrodes 410. The channels of the conductor organizer 452D extend along the spacing 492 between the first and second columns $414_1$, $414_2$. At least one wire conductor received by the conductor organizer 452D may be terminated to a respective electrode 410 of the first column $414_1$ and at least one wire conductor received by the conductor organizer 452D may be terminated to a respective electrode 410 of the second column $414_2$. Moreover, at least one wire conductor received by the conductor organizer 452D may extend through a distal opening 468 of the conductor organizer 452D and be terminated to a respective electrode 410 of the first column $414_1$ or a respective electrode 410 of the second column $414_2$.

FIGS. 10 and 11 illustrate different configurations of multi-dimensional arrays and conductor organizers. It is contemplated that a variety of other configurations of multi-dimensional array and shapes of conductor organizers may be used. By selecting the configuration of the multi-dimensional array, the shape of the conductor organizers, the number of channels, and the depth and locations of the side openings, the conductor organizers may be configured to provide openings (e.g., side openings or distal openings) that render handling the wire conductors during assembly easier. For example, in particular embodiments, the conductor organizers may be configured to provide openings (e.g., side openings or distal openings) that are adjacent to respective electrodes. An opening may be adjacent to a respective electrode if (a) no other opening for a wire conductor is closer to the respective electrode and (b) the wire conductor extending through the opening does not cross over another electrode.

It should be understood that one or more embodiments include a conductor organizer having at least one opening that is adjacent to the respective electrode(s) and at least one opening that is not adjacent to the respective electrode(s). In some embodiments, a majority of the openings are adjacent to the electrodes. In other embodiments, however, all or a majority of the openings are not adjacent to respective electrodes. Nonetheless, such embodiments may retain the wire conductors for a designated length thereby making it easier to control the plurality of wire conductors during assembly.

Also shown in FIG. 11, the first organizer ends 464 of the different conductor organizers may have different shapes. For example, the first organizer end 464 of the conductor organizer 452A is shaped to face generally toward the distal end of the lead body. The first organizer ends 464 of the conductor organizer 452B, 452C, and 452D are flat ends that extend transverse to a length of the conductor organizer. The first organizer end 464 of the conductor organizer 452E is shaped to face generally toward the distal end of the lead body. In such embodiments, it may be easier and/or require less time for inserting the wire conductors, such as those that are positioned in a splayed configuration as described herein.

Figure 12B:
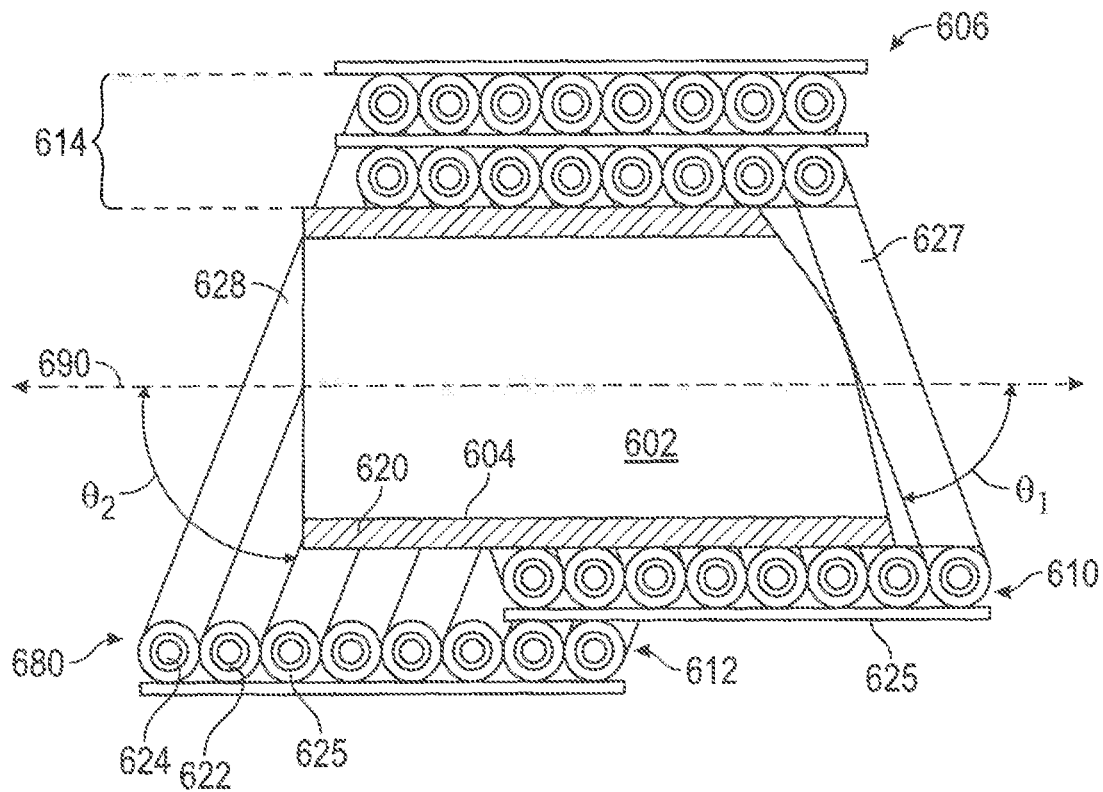
FIG. 12B is a cross-section of a lead body in accordance with another embodiment.

FIGS. 12A and 12B illustrate side cross-sections of respective lead bodies that may each be used in accordance with an embodiment. Lead bodies of some embodiments may be similar to lead bodies described in U.S. Patent Application Publication No. 2017/0080213, which is hereby incorporated by reference in its entirety. FIG. 12A is a side cross-section of the lead body 206. The lead body 206 includes a plurality of wire conductors 380. The lead body 206 is symmetric and includes one or more lumen 402 configured to receive a guide wire, stylus, or other device to facilitate implant of the lead body 206. A longitudinal axis 490 extends through a geometric center of the lumen 402. The lumen 402 is defined by and surrounded by an inner sheath 404 and an outer sheath 406. The inner and outer sheaths 404 and 406 enclose a first (or inner) winding 411 and a second (or outer) winding 413 of the wire conductors 380.

The first and second windings 411, 413 form a multi-layer coil 415 in which each of the first and second windings 411, 413 is wound about the lumen 402 and extends at least partially along a length of the lead body 206. The first winding 411 includes multiple winding turn segments that are wound about the lumen 402 in a first direction 417 about the lumen 402. The second winding 413 includes multiple winding turn segments that are wound about the first winding 411 in a second direction 418 about the lumen 402. Each wire conductor 380 may be helically wrapped along the lead body 206.

The turn segments 427 of the inner winding 411 are wound about the lumen 402 at a designated pitch angle (also referred to as a condensed pitch angle) relative to the longitudinal axis 490. The pitch angle represents the rise over run. For example, the turn segments 427 are oriented at an acute pitch angle $\Theta_1$ of between 30 and 50° relative to the longitudinal axis 490. As a further example, the turn segments 427 may be oriented at an acute pitch angle $\Theta_1$ of approximately 30°. The turn segments 428 of the second winding 413 are wound about the first winding 411 and the lumen 402 at a designated pitch angle relative to the longitudinal axis 490. For example, the turn segments 428 are oriented at an acute pitch angle $\Theta_2$ of between 30 and 50° relative to the longitudinal axis 490. As a further example, the turn segments 428 may be oriented at an acute pitch angle $\Theta_2$ of approximately 30°. The first and second pitch angles $\Theta_1$ and $\Theta_2$ may be the same (e.g., common) or may be different, depending upon various factors, such as the difficulty of manufacture, the size of the wire conductors 380 for the first and second windings 411, 413, which may be different and, the number of windings, and a level of elasticity desired in the lead body. The pitch angles $\Theta_1$, $\Theta_2$ may be adjusted, based on the degree to which the pitch angle renders the first and second windings 411, 413 difficult to manufacture.

The inner sheath 404 may comprise a tubular low-friction interior layer of a relatively high durometer, low friction, polymer-based material such as a thermoplastic polyurethane elastomer or other low-friction material configured to accommodate (and permit free movement of) a stylet or other guide device within the lumen 402. An outer surface of the inner sheath 404 may be coated with a layer 420 of an elastomeric polymer, such as a thermoplastic polyurethane elastomer. A durometer hardness (shore) for the material used to make the inner sheath 404 or the material used to make the layer 420 may be, for example, 50 or more using the ASTM D 2240 testing method.

Each of the wire conductors 380 is an insulated conductor having an insulation layer 422 that surrounds a metal conductor 424. The insulation layer 422 may be, for example, ethylene tetrafluoroethylene (ETFE) which has a relatively high melting temperature and high resistance properties. Optionally, the insulation layer 422 may be further coated with a jacket layer 425 (e.g., biocompatible layer), such as a thermoplastic polyurethane elastomer. In FIG. 12A, the first and second windings 411, 413 of the wire conductors 380 have been reflowed such that the jacket layers 425 of the wire conductors 380 join one another. The layer of combined material from the jacket layers 425 may be referred to as a bonding layer because the material holds the wire conductors of the same winding together.

Optionally, the wire conductors of a respective winding may be unwound as a group. The bonding material and the wire conductors of the respective group may form a conductor layer. For example, the first winding 411 and the bonding material formed from the combined jacket layers 425 form a first conductor layer. The second winding 413 and the bonding material formed from the combined jacket layers 425 form a second conductor layer. The bonding material holds the respective wire conductors side-by-side.

FIG. 12B is a side cross-section of a lead body 606, which may include similar or identical features as the lead body 206 (FIG. 12A). For example, the lead body 606 includes a plurality of wire conductors 680. The lead body 606 is symmetric and includes one or more lumen 602. A longitudinal axis 690 extends through a geometric center of the lumen 602. The lumen 602 is defined by and surrounded by an inner sheath 604. Optionally, an outer surface of the inner sheath 604 may be coated with a layer 620 of an elastomeric polymer, such as a thermoplastic polyurethane elastomer. A first (or inner) winding 610 and a second (or outer) winding 612 of the wire conductors 680 are wound about the lumen 602.

The first and second windings 610, 612 form a multi-layer coil 614 in which each of the first and second windings 610, 612 is wound about the lumen 602 and extends at least partially along a length of the lead body 606. The first winding 610 includes multiple winding turn segments 627 that are wound about the lumen 602 in a first direction (e.g., clockwise as the wire conductors 680 move toward the distal end of the lead body). The second winding 612 includes multiple winding turn segments 628 that are wound about the first winding 610 and the lumen 602 in an opposite second direction (e.g., counter-clockwise as the wire conductors 680 move toward the distal end of the lead body). Each wire conductor 680 may be helically wrapped along the lead body 606.

The turn segments 627 of the inner winding 610 are wound about the lumen 602 at a designated pitch angle (also referred to as a condensed pitch angle) relative to the longitudinal axis 690. For example, the turn segments 627 are oriented at an acute pitch angle $\Theta_1$ of between 30 and 50° relative to the longitudinal axis 690. The turn segments 628 of the second winding 612 are wound about the first winding 610 and the lumen 602 at a designated pitch angle relative to the longitudinal axis 690. For example, the turn segments 628 are oriented at an acute pitch angle $\Theta_2$ of between 30 and 50° relative to the longitudinal axis 690. The first and second pitch angles $\Theta_1$ and $\Theta_2$ may be the same (e.g., common) or may be different.

The wire conductors 680 may be similar or identical to the wire conductors 380 (FIG. 12A). The wire conductor 680 is an insulated conductor having an insulation layer 622 that surrounds a metal conductor 624. Optionally, the wire conductors 680 may be coupled to a lead backing 625. The lead backing 625 may comprise a bonding material and hold the individual wire conductors 680 of a winding in a substantially fixed position with respect to one another, thereby forming a conductor layer. As shown in FIG. 12B, each of the first and second windings 610, 612 is held by a respective lead backing 625 such that first and second conductor layers are formed. The lead backing 625 may function as an outer sheath in some embodiments. Optionally, an outer sheath (not shown) may surround the second winding 612.

Figure 13:
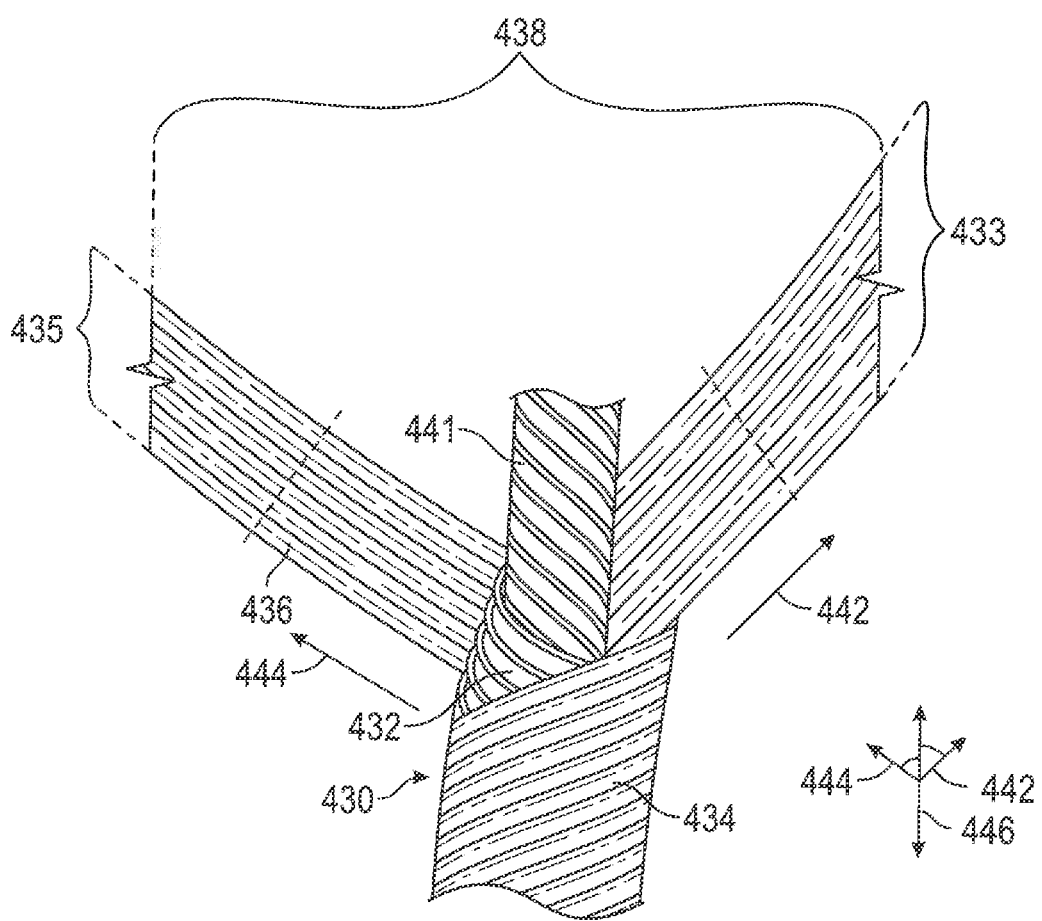
FIG. 13 depicts an end of a lead body in accordance with an embodiment in which two windings of wire conductors form a splayed or butterfly configuration.

FIG. 13 depicts an image of a distal end of a lead body 430, which may be similar to the lead body 206 (FIG. 12A) or similar to the lead body 606 (FIG. 12B). The lead body 430 includes first and second windings 432, 434 of wire conductors 436 that are wrapped about an inner sheath 441. At the distal end, the first and second windings 432, 434 may be unwound to form unwound groups 433, 435, respectively. When the wire conductors 436 are joined by a bonding material (e.g., thermoplastic polyurethane polymer), the unwound groups 433, 435 may be referred to as conductor layers. For example, the unwound group 433 and the corresponding bonding material may form a first conductor layer. The unwound group 435 and the corresponding bonding material may form a second conductor layer.

The unwound groups 433, 435 include segments of the wire conductors 436 that project away from the inner sheath 441 in first and second directions 442, 444, respectively, such that the lead body 430 has a splayed or butterfly configuration 438. As used herein, a "splayed configuration" or "butterfly configuration" includes groups of wire conductors (or conductor layers) that project away from the lumen or inner sheath in different directions. For example, the unwound group 433 (or first conductor layer) of the first winding 432 (or first conductor layer) projects in a first direction 442 along the lead body 430, and the unwound group 435 of the second winding 434 (or second conductor layer) projects in a second direction 444 along the lead body 430. The first and second directions 442, 444 may form an acute angle with respect to a longitudinal axis 446. Values of the acute angles may be similar to the values of the designated pitch angles. In such embodiments, the lead body 430 may have only a single inner sheath 441 or lumen.

As described above, the individual wire conductors may be held together by a bonding material. For example, in FIG. 13, each of the wire conductors 436 of the first and second windings 432, 434 is surrounded by an additional layer of material, such as a jacket layer 425 (FIG. 12B). The additional jacket layers may be reflowed to join one another. The combined jacket layers may be referred to as a bonding layer that comprises the bonding material of the jacket layers 425. In such instances, the unwound groups 433, 435 of the first and second windings 432, 434 may form respective conductor layers in which the wire conductors of each winding are held together by the bonding material.

Optionally, the bonding material that holds the wire conductors together may exist along each of the first and second windings 432, 434 for a distance. As indicated by the dashed lines, the bonding material may be removed after this distance to free the wire conductors 436 from the groups. The bonding material may be removed from the first and second windings 432, 434 so that the individual wire conductors 436 may be handled for inserting into the conductor organizers (not shown). The bonding material may be removed by applying a chemical solvent that removes the material of the bonding material. In such embodiments, a first cross-section of the lead paddle (not shown) that includes the first winding 432 prior to the dashed line will have the bonding material. The bonding material may be surrounded by another material, such as the material of the backing layer. But a second cross-section of the lead paddle that includes the first winding 432 after the dashed line will essentially not have the bonding material.

For embodiments that include conductor layers, the wire conductors of a conductor layer are separated from one another and inserted through a respective channel. In such embodiments, a cross-section of the lead paddle may include material other than the bonding material between the individual wire conductors.

Figure 14:
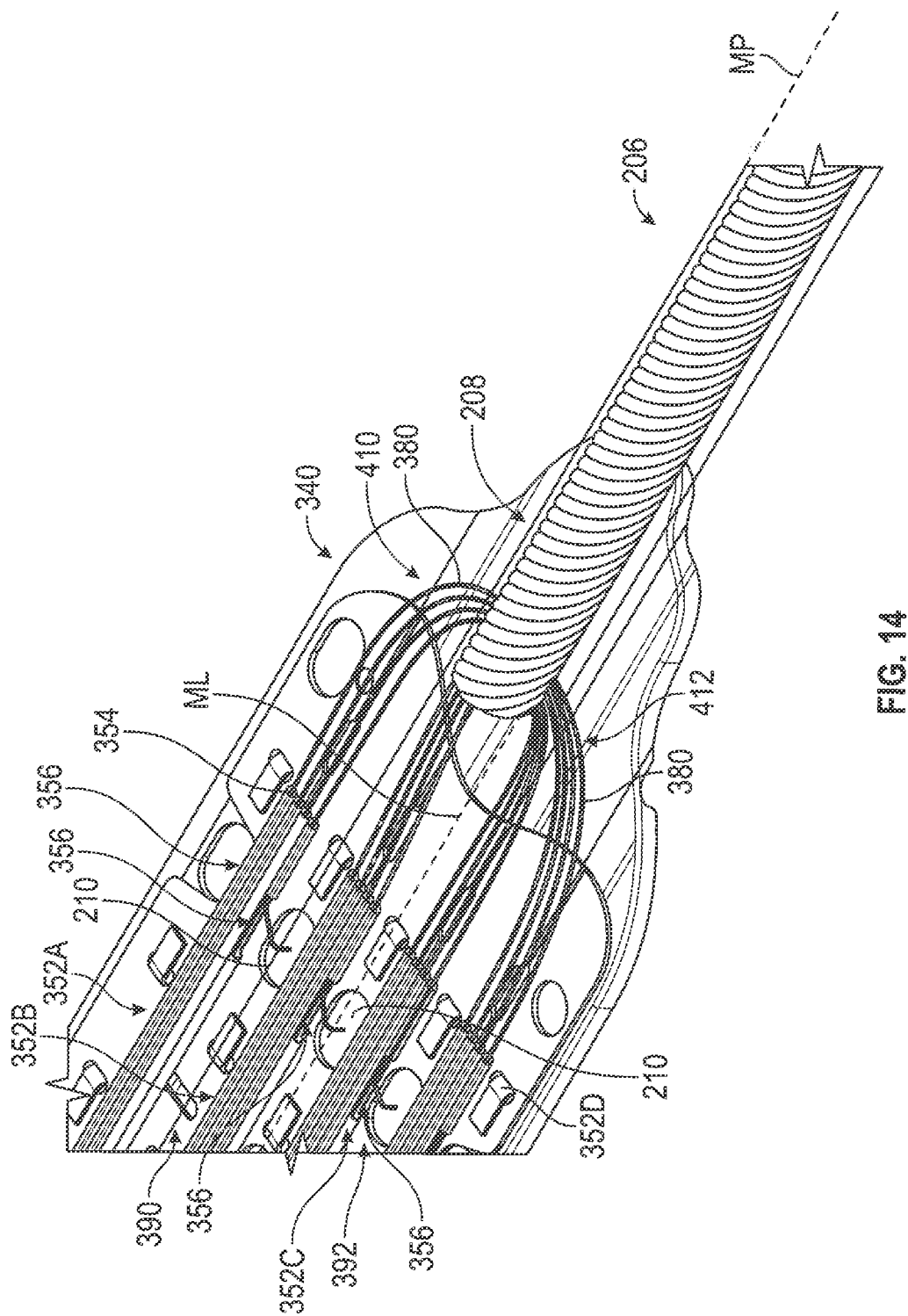
FIG. 14 is an enlarged perspective view of the multi-layered structure and an end of the lead body, in accordance with an embodiment, in which two windings of wire conductors form a splayed or butterfly configuration.

FIG. 14 is an enlarged perspective view of the multi-layered structure 340 and the distal end 208 of the lead body 206. At 260 of the method 250 (FIG. 4), the distal end 208 of the lead body 206 may be positioned onto the multi-layered structure 340. Prior to positioning, at 260, the distal end 208 of the lead body 206 or prior to positioning, at 258, the conductor organizers 352A-352D, the wire conductors 380 may be inserted through the corresponding channels 354 of the conductors organizers 352A-352D. Segments of the wire conductors 380 may be moved (e.g., pushed or pulled) through the respective side openings 356 or distal openings 368 (FIG. 9) and positioned adjacent to the respective electrodes 210.

Figure 15:
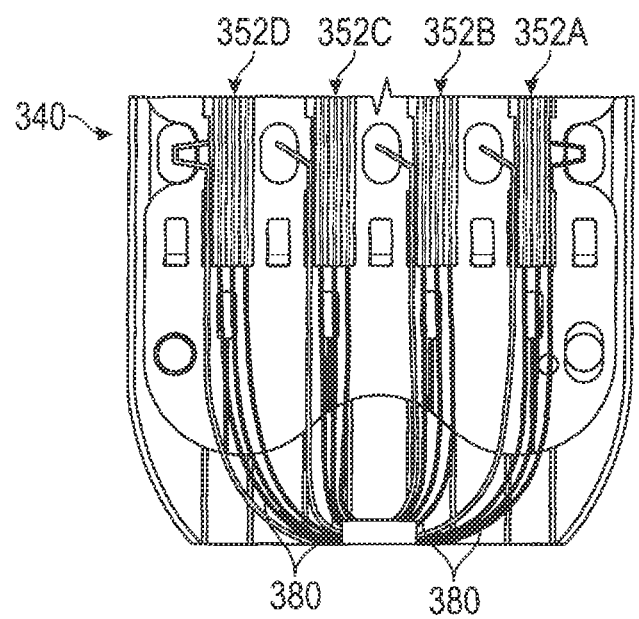
FIG. 15 is an enlarged plan view of the multi-layered structure illustrating an arrangement of the wire conductors that form the splayed configuration.

In particular embodiments, the first and second windings 410, 412 of the lead body 206 are arranged in the splayed (or butterfly) configuration in FIG. 14 (and FIG. 15). The lead body 206 may be positioned onto the multi-layered structure 340. The multi-layered structure 340 may have a first lateral section 390 and a second lateral section 392. As shown, the first and second lateral sections 390, 392 are separated by a midline M$_L$ (or midplane M$_P$) of the multi-layered structure 340. Because of the splayed configuration, the wire conductors 380 of the first winding 411 are directed toward the first lateral section 390, and the wire conductors 380 of the second winding 413 are directed toward the second lateral section 392.

Figure 16:
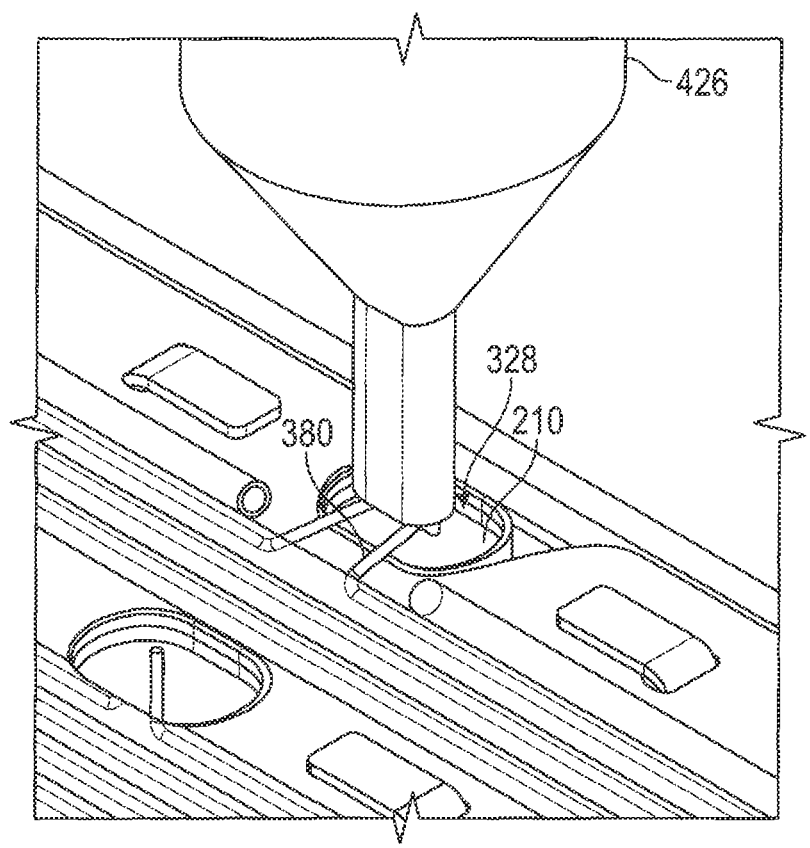
FIG. 16 depicts a wire conductor being mechanically and electrically coupled to an electrode in accordance with an embodiment.

FIG. 15 is an enlarged plan view of the multi-layered structure 340 having the wire conductors 380 and the conductor organizers 352A-352D thereon, and FIG. 16 depicts a wire conductor 380 being mechanically and electrically coupled to the respective electrode 210. At 262 of the method 250 (FIG. 4), the wire conductors 380 are electrically coupled to the respective electrodes 210. The wire conductors 380 extend through the conductor passages 328 (FIG. 16) and are positioned onto the electrode 210. The wire conductors 380 may be welded to the respective electrodes 210. A welding electrode 426 is positioned over the wire conductor 380. A combination of heat and force may displace the insulation layer 422 (FIG. 12A) and allow the metal conductor 424 (FIG. 12A) to be welded to the electrode 210. It is contemplated that other methods of electrically coupling the wire conductors 380 to the electrodes 210 may be used.

Figure 17:
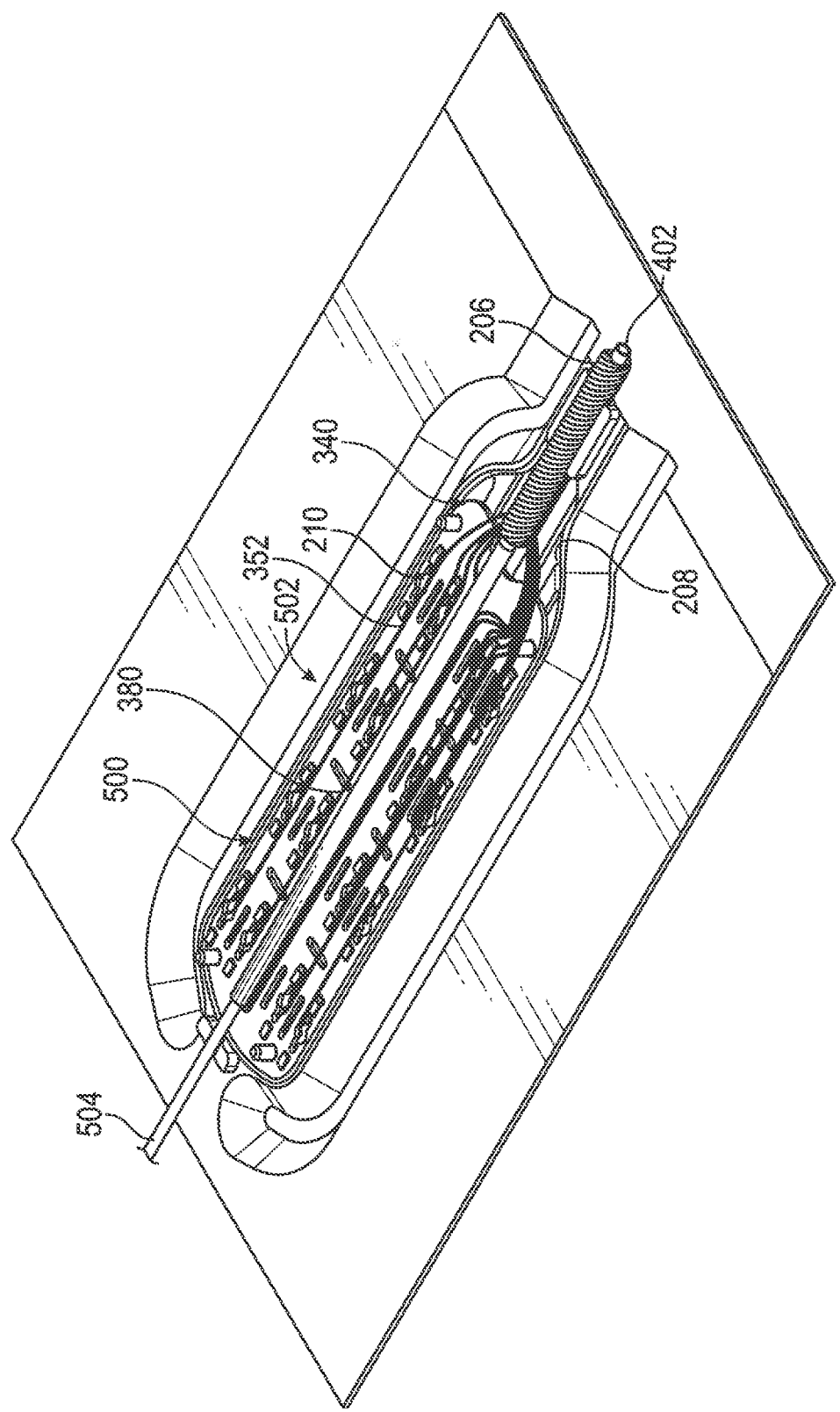
FIG. 17 depicts a sub-assembly positioned within a mold cavity prior to a backing layer being added, in accordance with an embodiment.

FIG. 17 depicts a sub-assembly 500 positioned within a mold cavity 502 prior to the backing layer 218 (FIG. 2) being added. The method 250 (FIG. 4) also includes inserting an elongated mandrel 504, at 264, through the lumen 402 of the lead body 206. In the illustrated embodiment, the mandrel 504 extends entirely through the cavity 502. The sub-assembly 500 includes the multi-layer structure 340, the conductor organizers (referenced generally as 352), the wire conductors 380 electrically coupled to the electrodes 210, the distal end 208 of the lead body 206, and the mandrel 504. The method 250 (FIG. 4) also includes positioning, at 266, the sub-assembly 500 within the cavity 502 and molding, at 268, the backing layer 218 to the multi-layered structure 340. The backing layer 218 may comprise, for example, a high consistency rubber (HCR) silicone, also known as gum stock silicone. After removing the lead paddle 200 from the cavity 502, the contact side 202 (FIG. 2), among other things, may be cleaned, at 270.

Figure 19:
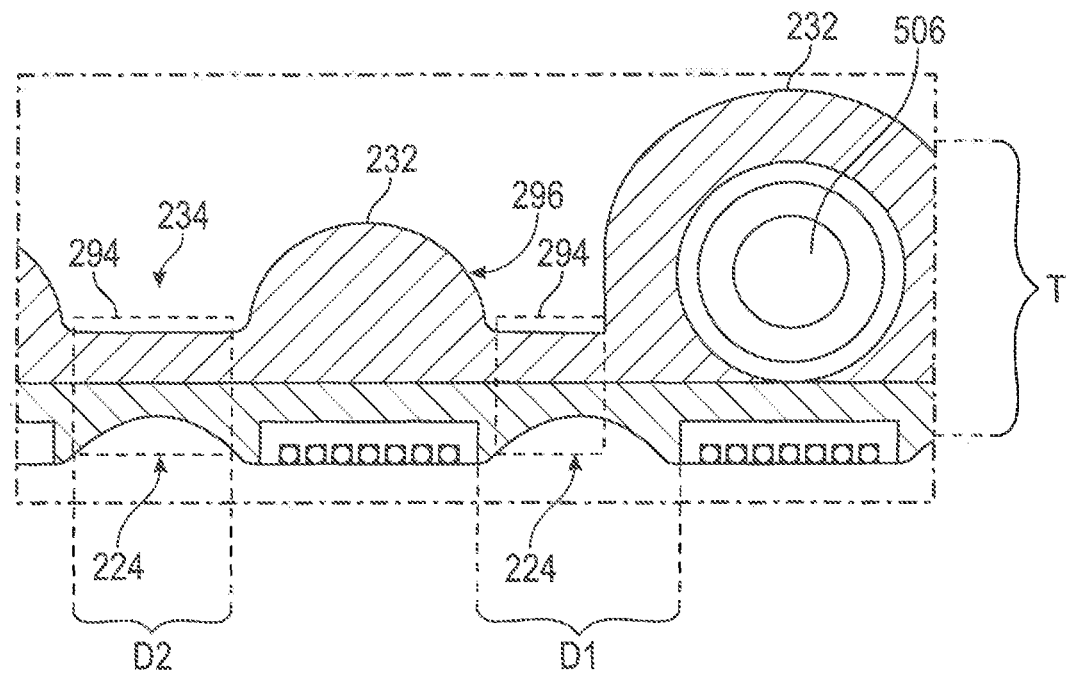
FIG. 19 illustrates a cross-section of the lead paddle taken along lines 19-19 in FIG. 3.

FIG. 18 is an end view of the lead paddle 200, and FIG. 19 illustrates a cross-section of the lead paddle 200 taken along lines 19-19 in FIG. 3. As shown, the lead paddle 200 has a thickness T that is determined by the flexible layer 216 and the backing layer 218. Optionally, an opening 506 left by the mandrel 504 (FIG. 17) may be filled. As shown, the backing layer 218 is shaped to define the raised portions 232 and the recessed portions 234 along the back side 204. The raised portions 232 are separated by the recessed portions 234, and the recessed portions 234 are separated by the raised portions 232. In the illustrated embodiment, the raised portions 232 are elongated ridges that extend parallel to one another. The recessed portions 234 are elongated grooves or open-sided channels that extend parallel to one another.

Also shown in FIG. 18, the lead paddle 200 may be divided into a first lateral section 590 and second lateral section 592. As shown, the first and second lateral sections 590, 592 of the lead paddle 200 are separated by the midline M$_L$ (or the midplane M$_P$).

As shown in FIG. 19, in some embodiments, at least some of the recessed portions 234 of the backing layer 218 and at least some of the recessed regions 224 of the flexible layer 216 align with one another at thin sections 294 of the lead paddle 200. At least some of the raised portions 232 of the backing layer 218 and at least some of the raised regions 222 of the flexible layer 216 align with one another at thick sections 296 of the lead paddle 200. The aligned recessed portions 234 and recessed regions 224 may enable flexing by the lead paddle 200. The lead paddle 200 may more readily flex about the thin sections 294 than the thick sections 296. In some embodiments, the raised portions 232 may engage scar tissue within the epidural space that reduces the likelihood of migration.

By way of example, a spacing 295 between adjacent electrodes 210 may be 0.039 inches (or 0.9906 mm). A width D$_2$ of the between recessed region 224 may be 0.030 inches (0.762 mm). However, it should be understood that alternative embodiments may have other pitches or widths. In some embodiments, the spacing 295 exists between adjacent columns 360 such that the columns 360 are separated by the spacing 295. This spacing 295 is similar to the spacing 492 (FIG. 11). The spacing 295 is a region of the paddle body 212 (FIG. 2) that exists between the electrodes 210 (FIG. 2). The spacing 295 may include portions of the paddle body 212 and is not required to be empty space, although it may include empty space.

Figure 20:
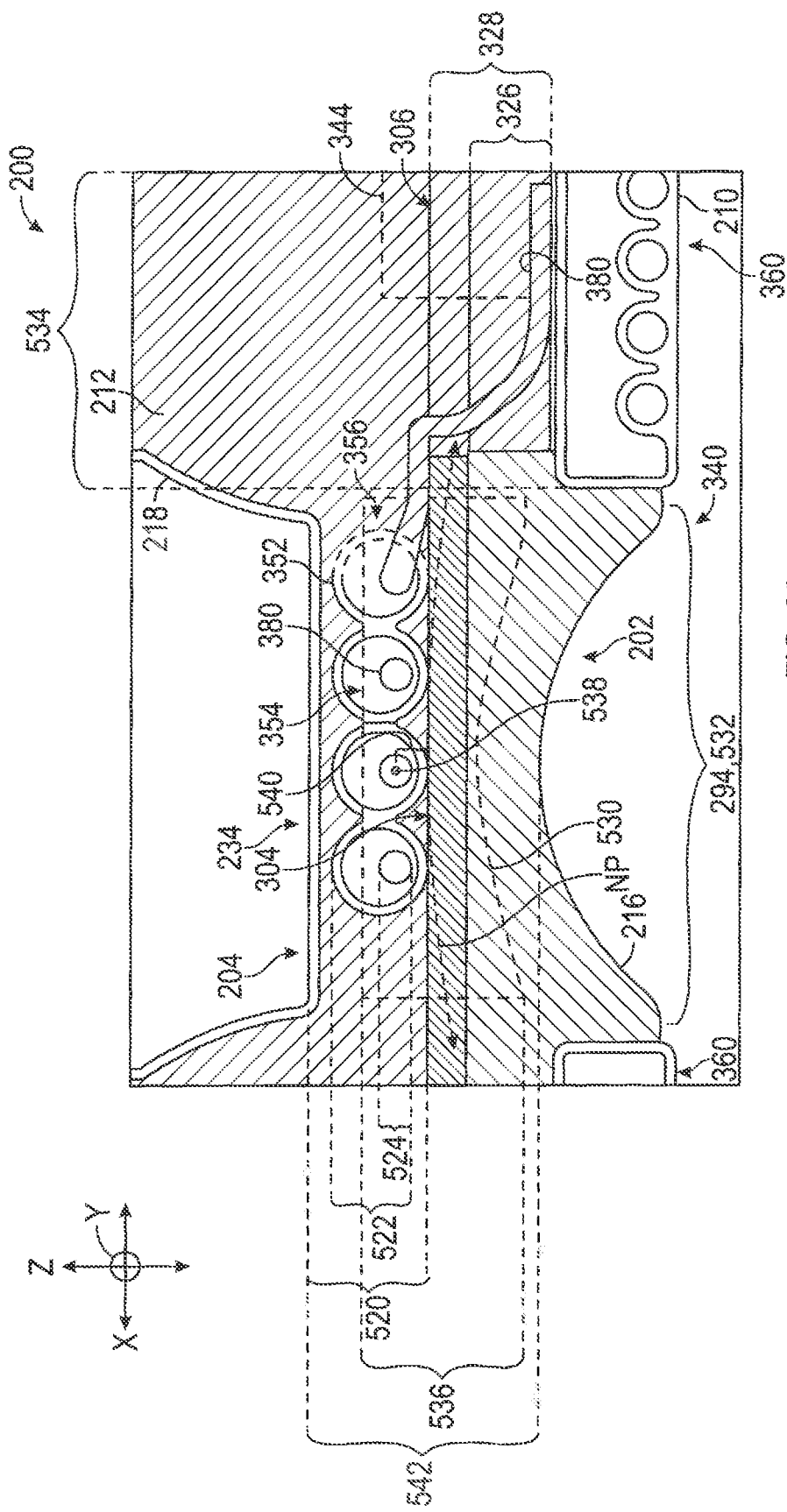
FIG. 20 is an enlarged cross-section of the lead paddle that illustrates a neutral longitudinal force envelope (NLFE) of an embodiment.

FIG. 20 is a cross-section of the lead paddle 200 that includes one of the conductor organizers 352 and a plurality of the wire conductors 380 received within respective channels 354. In the illustrated embodiment, the channels 354 of the conductor organizer 352 extend along and parallel to the second side surface 304 of the inner frame 220. The channels 354 of the conductor organizer 352 may extend along the spacing 295 between the columns 360 of the electrodes 210. One of the wire conductors 380 extends through a side opening 356 of the conductor organizer 352 and into a conductor passage 328 of the lead paddle 200. The wire conductor 380 is terminated to an electrode 210. As shown, a frame window 306 of the inner frame 220 and a layer window 326 of the flexible layer 216 are aligned to form the conductor passage 328. After the backing layer 218 is applied to the multi-layered structure 340, the material of the backing layer 218 may be disposed within the conductor passage 328. At least a portion of the channels 354 may be filled with the material of the backing layer 218.

The recessed portion 234 of the backing layer 218 where the conductor organizer 352 is disposed has a layer thickness 520. The conductor organizer 352 has an organizer height 522, and the wire conductor 380 has a diameter 524. The layer thickness 520 may be configured to accommodate the organizer height 522. For example, the layer thickness 520 may be at least 10% greater than the organizer height 522 or, more particularly, at least 20% greater than the organizer height 522. In some embodiments, the layer thickness 520 is at least 0.051 mm (0.002 in) greater than the organizer height 522.

The layer thickness 520 of the recessed portion 234 may be, for example, at most 0.508 mm (0.020 in). In certain embodiments, the layer thickness 520 at the recessed portion 234 may be, for example, at most 0.381 mm (0.015 in) or, more particularly, at most 0.305 mm (0.012 in) or, more particularly, at most 0.254 mm (0.010 in). The organizer height 522 of the conductor organizer 352 prior to deformation may be, for example, at most 0.381 mm (0.015 in). In certain embodiments, the organizer height 522 prior to deformation may be, for example, at most 0.305 mm (0.012 in) or, more particularly, at most 0.229 mm (0.009 in) or, even more particularly, at most 0.203 mm (0.008 in). The diameter 524 of the wire conductor 380 may be, for example, at most 0.125 mm (0.050 in). More particularly, the diameter 524 of the wire conductor 380 may be, for example, at most 0.090 mm (0.035 in).

It should be understood that the above upper limits and relationships are provided as examples that may be used with some embodiments. Embodiments may have upper limits or relationships defined by values that are greater than or less than the values provided above.

In FIG. 20, the conductor organizer 352 is shown in an uncompressed or non-deformed condition. In some embodiments, the conductor organizer 352 may be compressed and deformed (e.g., crushed) during manufacture such that the size of the channel 354 is reduced. Specifically, the organizer height 522 may be reduced and the channel 354 may be collapsed around the wire conductor 380. In some embodiments, the material of the backing layer 218 may flow into the channel 354 during the molding, at 268, and solidify therein. Air pockets may or may not exist within the channels 354 after molding at 268.

Optionally, embodiments set forth herein have wire conductors that are positioned within the lead paddle (or the paddle body) to reduce stresses experienced by the wire conductors when the lead paddle is flexed. The wire conductors may be positioned along or near a neutral plane. A neutral plane is a conceptual plane that is used in engineering design. When a structure is flexed or bent in a direction that is transverse to the neutral plane, the neutral plane separates one region that is in compression and one region that is in tension.

As describe above, embodiments may be configured to reduce the likelihood that the wire conductors will break and/or separate from the electrodes. As such, the wire conductors may be positioned within the NLFE for at least a portion of the length of the lead paddle. When the lead paddle is flexed or bent, the NLFE may experience a compression stress on one side of the neutral plane that is less than the compression stress experienced outside the NLFE. On the other side of the neutral plane, the NLFE may experience a tensile stress that is less than the tensile stress experienced outside the NLFE. Lead paddles may be configured to control the amount of stress (whether tensile or compression) and thereby reduce the likelihood that the connections to the electrodes will fail.

As shown in FIG. 20, a portion of the NLFE is represented by a box 530. Because the lead paddle 200 or the paddle body 212 can have a complex three-dimensional shape (as partially shown in FIG. 20), the NLFE 530 is not necessarily a planar structure having two parallel sides and a uniform thickness. The NLFE 530 includes a neutral plane NP of the paddle body 212 or the lead paddle 200. The neutral plane NP extends substantially parallel to the XY plane.

The wire conductors 380 may be positioned within the lead paddle 200 to modulate the stresses experienced by the wire conductors 380 due to flexing. For example, when the lead paddle 200 is flexed transverse to the Y axis (or transverse to the longitudinal axis 290 (FIG. 3)) such that a distal section is bent downward relative to the XY plane, the portion of the lead paddle 200 that is below the neutral plane NP near the bend is compressed. The portion of the lead paddle 200 that is above the neutral plane NP near the bend is stretched. The NLFE 530 experiences a compression stress that is less than the compression stress experienced by the lead paddle 200 outside of the NLFE 530. The NLFE 530 experiences a tensile stress that is less than the tensile stress experienced by the lead paddle 200 outside of the NLFE 530. The stresses within the NLFE 530 may be controlled to reduce the likelihood that the electrical connections to the electrodes will be broken.

Conversely, when the lead paddle 200 is flexed transverse to the Y axis (or transverse to the longitudinal axis 290 (FIG. 3)) such that a distal section is bent upward relative to the XY plane, the portion of the lead paddle 200 that is below the neutral plane NP near the bend is stretched. The portion of the lead paddle 200 that is above the neutral plane NP near the bend is compressed. The NLFE 530 experiences a compression stress that is less than the compression stress experienced by the lead paddle 200 outside of the NLFE 530. The NLFE 530 experiences a tensile stress that is less than the tensile stress experienced by the lead paddle 200 outside of the NLFE 530. Again, the stresses within the NLFE 530 may be controlled to reduce the likelihood that the electrical connections to the electrodes will be broken.

In some embodiments, the inner frame 220 at least partially determines a location of the NLFE 530. More specifically, properties of the inner frame 200, when secured to the backing layer 218, may determine a location of the NLFE 530 within the lead paddle 200. In such instances, a wire conductor may be within the NLFE when a center of the wire conductor is within a designated distance from the inner frame. For example, the wire conductor 380 is within the NLFE 530 when a center 538 of the wire conductor 380 is separated from the second side surface 304 of the inner frame 220 by a distance 540 that is at most two-and-a-half times (2.5×) the diameter 524 of the wire conductor 380. In particular embodiments, the wire conductor 380 is within the NLFE 530 when a center 538 of the wire conductor 380 is separated from the second side surface 304 of the inner frame 220 by a distance 540 that is at most two times (2×) the diameter 524 of the wire conductor 380. In more particular embodiments, the wire conductor 380 is within the NLFE 530 when the distance 540 is at most one-and-a-half times (1.5×) the diameter 524 of the wire conductor 380.

The minimum thickness 542 is the shortest distance between the contact side 202 and the back side 204. Optionally, the NLFE 530 is located within a middle one-half of a minimum thickness 542 of the thin section 294. More specifically, at least one quarter of the thickness of the thin section 294 may be above the NLFE 530 and at least one quarter of the thickness may be below the NLFE 530. In more particular embodiments, the NLFE 530 is located within a middle one-third of a minimum thickness 542 of the thin section 294. More specifically, at least one third of the thickness of the thin section 294 may be above the NLFE 530 and at least one third of the thickness may be below the NLFE 530.

Optionally, the NLFE 530 may have a thickness 536 that is at most five times (5×) a diameter of the wire conductor. In particular embodiments, the NLFE 530 may have a thickness 536 that is at most three times (3×) a diameter of the wire conductor or, more particularly, a thickness 536 that is at most two times (2×) a diameter of the wire conductor.

In some embodiments, at least one or more sections of the inner frame 220 (or the entire inner frame 220) may be positioned within or adjacent to the NLFE 530. For example, the second side surface 304 of the inner frame 220 may include neutral force lanes 532 that are disposed within or adjacent to the NLFE 530. For embodiments that include the thin sections 294, the neutral force lanes 532 may extend along and through the thin sections 294 of the lead paddle 200. In FIG. 20, the neutral force lane 532 extends between columns 360 of the electrodes 210. The second side surface 304 of the inner frame 220 may also include a wire-void area 534. In FIG. 20, the wire-void area 534 of the inner frame 220 aligns with the non-contact faces 345 of the electrodes 210 of a single column 360.

In the illustrated embodiment, the neutral force lanes 532 are linear and extend between the columns 360. In other embodiments, the neutral force lanes 532 may curve and/or cross over a column without crossing over the wire-void areas 534.

In particular embodiments, the conductor organizers 352 route the wire conductors 380 along the neutral force lanes 532 so that stresses experienced by the wire conductors 380 are not excessive. Alternatively or in addition to the above, the conductor organizers 352 may prevent the wire conductors 380 from crossing over one another and crossing over the wire-void areas 534 (or over the projections 344, 346 (FIG. 8A)). As such, the likelihood of the wire conductors breaking or otherwise causing the electrodes to fail may be reduced.

A wire conductor is not required to extend along the NLFE for the entire length of the lead paddle. In some embodiments, a wire conductor may reside within the NLFE if a center of the wire conductor is separated from the second side surface of the inner frame by at most a predetermined distance (e.g., at most 2.5× or 2× of the diameter) for at least half of the length of the lead paddle. In some embodiments, a wire conductor may reside within the NLFE if a center of the wire conductor is separated from the second side surface of the inner frame by at most a predetermined distance (e.g., at most 2.5× or 2× of the diameter) for at least the last half of the length of the lead paddle. In other words, the half of the lead paddle that includes a distal end of the lead paddle. In particular embodiments, a wire conductor may reside within the NLFE if a center of the wire conductor is separated from the second side surface of the inner frame by at most a predetermined distance (e.g., at most 2.5× or 2× of the diameter) for at least three quarters of the length of the lead paddle including the distal end of the lead paddle.

In some embodiments, the lead paddles set forth herein may be manufactured without conductor organizers. In such embodiments, the wire conductors may be positioned, as described herein, such that the wire conductors extend longitudinally between columns of the electrodes and/or the wire conductors do not cross over one another and/or the wire conductors do not cross over the electrodes (e.g., projections of the electrodes). For example, the wire conductors may be clamped at one or both ends of the paddle body as the backing layer is molding.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit execute a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable stimulation lead for stimulation of neural tissue of a patient, comprising:

an elongated lead body having distal and proximal ends and wire conductors extending therebetween; and a paddle structure adapted to be implanted adjacent to neural tissue for electrical stimulation, the paddle structure comprising a flexible polymer body, electrodes arranged in a multi-dimensional pattern and positioned along a contact side of the flexible polymer body, and a plurality of sets of microtubes with each microtube having an inner lumen, the plurality of sets of microtubes extending along a side of the flexible polymer body opposite to the contact side and configured to facilitate positioning the wire conductors;

wherein (1) the electrodes are electrically coupled to the wire conductors of the lead body through wires positioned within the inner lumens of the plurality of sets of microtubes, (2) each set of microtubes are positioned to extend along the paddle structure, and (3) the polymer body of the paddle structure flexes transversely about its longitudinal axis and the plurality of sets of microtubes are arranged generally parallel to the longitudinal axis.

2. The stimulation lead of claim 1 wherein distal ends of the conductor wires of the lead body are placed within the inner lumens of the plurality of sets of microtubes and are directly electrically connected to the electrodes.

3. The stimulation lead of claim 1 wherein the electrodes are connected to the wire conductors of the lead body through one or more intermediate conductor elements.

4. The stimulation lead of claim 1, wherein each set of the plurality of sets of microtubes comprise multiple microtubes that are connected to one another in a side-by-side configuration.

5. The stimulation lead of claim 1, wherein the paddle structure comprises an inner frame having opposite first and second side surfaces and a polymer layer secured to the first side surface of the inner frame, the polymer layer defining a portion of the contact side of the lead paddle, the inner frame being more rigid than the polymer layer, and the plurality of sets of microtubes extend along the second side surface of the inner frame.

6. The stimulation lead of claim 1, wherein the electrodes are arranged in columns that extend longitudinally along the lead paddle and each set of the plurality of sets of microtubes extend longitudinally between adjacent columns of electrodes.

7. The stimulation lead of claim 6, wherein the columns include first and second columns that are adjacent to one another with a respective set of microtubes extending longitudinally between the first and second columns, wherein at least one of the wires within the inner lumen of one microtube of the respective set is connected to one of the electrodes of the first column and at least one of the wires within the inner lumen of one microtube of the respective set is connected to one of the electrodes of the second column.

8. The stimulation lead of claim 1, wherein the openings of the microtubes are positioned adjacent to the respective electrodes, the openings include at least one side opening and at least one distal opening, the distal opening is at an end of at least one set of microtubes, and the side opening is spaced apart from the at least one distal opening.

9. The stimulation lead of claim 1, wherein the sets of microtubes are arranged so that wires within the microtubes do not cross over each other on the paddle structure.

10. The stimulation lead of claim 1, wherein (1) the paddle structure comprises an inner frame enclosed within the flexible polymer body, (2) the inner frame comprises a plurality of grooves extending longitudinally along the frame, and (3) each set of the plurality of sets of microtubes is located below a respective groove of the inner frame to define a fold line about which the paddle structure flexes transversely relative to the longitudinal axis of the paddle structure.

11. A method of fabricating an implantable stimulation lead for provision of electrical stimulation to tissue of a patient, the method comprising:

providing a paddle structure adapted to be implanted adjacent neural tissue for electrical stimulation, the paddle structure comprising a flexible polymer body;

providing electrodes arranged in a multi-dimensional pattern and positioned along a contact side of the flexible polymer body;

providing a plurality of sets of microtubes with each microtube having an inner lumen on the flexible polymer body, the plurality of sets of microtubes extending along a side of the flexible polymer body opposite to the contact side and configured to facilitate positioning the wire conductors;

routing a wire through each respective microtube of the plurality of sets of microtubes; and electrically coupling the wires within plurality of sets of microtubes to respective electrodes positioned along a contact side of the flexible polymer body, wherein the polymer body of the paddle structure flexes transversely about its longitudinal axis and the plurality of sets of microtubes are arranged generally parallel to the longitudinal axis.

12. The method of claim 11 wherein the routing a wire through each respective microtube comprises inserting a separate respective conductor wire from a lead body through the inner lumen of each separate respective microtube.

13. The method of claim 11 further comprising:

forming a respective opening for each microtube of the plurality of sets of microtubes;

removing a portion of the wire from the inner lumen of each microtube; and electrically connecting the removed portion of the wire from each microtube to an electrode through the polymer body.

14. The method of claim 13 wherein the electrically connecting the removed portion of the wire comprises welding the removed portion of the wire to an electrode.

15. The method of claim 11 wherein the paddle structure comprises an inner frame having opposite first and second side surfaces, the electrodes are provided on the first side of the inner frame, and the plurality of sets of microtubes extend along the second side surface of the inner frame.

16. The method of claim 11 wherein the routing a conductor through each respective microtube comprises:

applying a chemical solvent to release segments of conductor wires bonded to first and second backing layers.

17. The method of claim 11, wherein each set of the plurality of sets of microtubes comprise multiple microtubes that are connected to one another in a side-by-side configuration.

18. The method of claim 11, wherein (1) the paddle structure comprises an inner frame, (2) the inner frame comprises a plurality of grooves extending longitudinally along the frame, (3) each set of the plurality of sets of microtubes is located below a respective groove of the inner frame to define a fold line where the paddle structure flexes transversely relative to the longitudinal axis of the paddle structure.

* * * * *